United States Patent
McGuckin, Jr. et al.

(10) Patent No.: US 8,591,541 B2
(45) Date of Patent: *Nov. 26, 2013

(54) VEIN FILTER

(75) Inventors: James F. McGuckin, Jr., Radnor, PA (US); James E. Bressler, Langhorne, PA (US); John H. Thinnes, Jr., Westfield, NJ (US); Stephen A. DeFonzo, Wayne, PA (US); Lindsay L. Carter, Wayne, PA (US)

(73) Assignee: Rex Medical L.P., Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/433,500

(22) Filed: Mar. 29, 2012

(65) Prior Publication Data

US 2012/0184986 A1   Jul. 19, 2012

Related U.S. Application Data

(63) Continuation of application No. 12/770,508, filed on Apr. 29, 2010, now Pat. No. 8,162,972, which is a continuation-in-part of application No. 11/978,821, filed on Oct. 30, 2007, now Pat. No. 8,366,736, which is a continuation of application No. 10/889,429, filed on Jul. 12, 2004, now Pat. No. 7,704,266, and a continuation-in-part of application No. 10/805,796, filed on Mar. 22, 2004, now Pat. No. 7,338,512, said application No. 12/770,508 is a continuation-in-part of application No. 11/801,547, filed on May 10, 2007, now Pat. No. 7,976,562, and a continuation-in-part of application No. 10/889,429, filed on Jul. 12, 2004, now Pat. No. 7,704,266.

(60) Provisional application No. 60/572,274, filed on May 18, 2004, provisional application No. 60/538,379, filed on Jan. 22, 2004, provisional application No. 60/818,202, filed on Jun. 30, 2006.

(51) Int. Cl.
*A61F 2/01* (2006.01)

(52) U.S. Cl.
USPC .......................................................... 606/200

(58) Field of Classification Search
USPC ......... 606/108, 113, 114, 127, 128, 159, 194, 606/200; 623/23.72
See application file for complete search history.

(56) References Cited

U.S. PATENT DOCUMENTS

| | | |
|---|---|---|
| 3,744,492 A | 7/1973 | Leibinsohn |
| 3,952,747 A | 4/1976 | Kimmell, Jr. |

(Continued)

FOREIGN PATENT DOCUMENTS

| | | |
|---|---|---|
| DE | 3429850 | 2/1986 |
| EP | 1707233 | 10/2006 |

(Continued)

OTHER PUBLICATIONS

B. Braun Medical. Inc. Vena Tech™ Vena Cava Filters, Feb. 2000.

(Continued)

*Primary Examiner* — Kathleen Holwerda
(74) *Attorney, Agent, or Firm* — Neil D. Gershon

(57) ABSTRACT

A vessel filter having a first region and a second region, the filter movable between a collapsed position for delivery to the vessel and an expanded position for placement within the vessel. The first region has a filter portion having a converging region to direct particles toward the center of the filter and includes a plurality of spaced apart filter struts. The struts each have a strut height defined as a distance between a first wall and a second wall. A plurality of hooks are at the second region, the hooks having a vessel penetrating tip and a width greater than the width of the strut from which it extends such that the penetrating tip portion of the hook extends beyond the first wall.

6 Claims, 35 Drawing Sheets

(56) References Cited

U.S. PATENT DOCUMENTS

| | | |
|---|---|---|
| 4,266,815 A | 5/1981 | Cross |
| 4,425,908 A | 1/1984 | Simon |
| 4,494,531 A | 1/1985 | Gianturco |
| 4,512,338 A | 4/1985 | Balko et al. |
| 4,619,246 A | 10/1986 | Molgaard-Nielsen et al. |
| 4,643,184 A | 2/1987 | Mobin-Uddin |
| 4,688,553 A | 8/1987 | Metals |
| 4,727,873 A | 3/1988 | Mobin-Uddin |
| 4,781,177 A | 11/1988 | Lebigot |
| 4,793,348 A | 12/1988 | Palmaz |
| 4,817,600 A | 4/1989 | Herms et al. |
| 4,832,055 A | 5/1989 | Palestrant |
| 4,957,501 A | 9/1990 | Lahille et al. |
| 4,990,156 A | 2/1991 | Lefebvre |
| 4,994,069 A | 2/1991 | Ritchart et al. |
| 5,059,205 A | 10/1991 | El-Nounou et al. |
| 5,133,733 A | 7/1992 | Rasmussen et al. |
| 5,152,777 A | 10/1992 | Goldberg et al. |
| 5,234,458 A | 8/1993 | Metals |
| 5,300,086 A | 4/1994 | Gory et al. |
| 5,324,304 A | 6/1994 | Rasmussen |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,531,788 A | 7/1996 | Dibie et al. |
| 5,591,197 A | 1/1997 | Orth et al. |
| 5,601,595 A | 2/1997 | Smith |
| 5,626,605 A | 5/1997 | Irie et al. |
| 5,634,942 A | 6/1997 | Chevillon et al. |
| 5,681,347 A | 10/1997 | Cathcart et al. |
| 5,683,411 A | 11/1997 | Kavteladze et al. |
| 5,690,671 A | 11/1997 | McGurk et al. |
| 5,709,704 A | 1/1998 | Nott et al. |
| 5,725,552 A | 3/1998 | Kotula et al. |
| 5,733,294 A | 3/1998 | Forber et al. |
| 5,733,329 A | 3/1998 | Wallace et al. |
| 5,746,767 A | 5/1998 | Smith |
| 5,755,779 A | 5/1998 | Horiguchi |
| 5,755,790 A | 5/1998 | Chevillon et al. |
| 5,776,162 A | 7/1998 | Kleshinski |
| 5,782,748 A | 7/1998 | Palmer et al. |
| 5,795,322 A | 8/1998 | Boudewijn |
| 5,800,457 A | 9/1998 | Gelbfish |
| 5,810,874 A | 9/1998 | Lefebvre |
| 5,836,968 A | 11/1998 | Simon et al. |
| 5,853,420 A | 12/1998 | Chevillon et al. |
| 5,893,869 A | 4/1999 | Barnhart et al. |
| 5,895,398 A | 4/1999 | Wensel et al. |
| 5,895,410 A | 4/1999 | Forber et al. |
| 5,911,717 A | 6/1999 | Jacobsen et al. |
| 5,938,683 A * | 8/1999 | Lefebvre ................ 606/200 |
| 5,968,071 A | 10/1999 | Chevillon et al. |
| 5,976,172 A | 11/1999 | Homsma et al. |
| 5,984,947 A | 11/1999 | Smith et al. |
| 6,007,558 A | 12/1999 | Ravenscroft et al. |
| 6,013,093 A | 1/2000 | Nott et al. |
| 6,036,702 A | 3/2000 | Bachinski et al. |
| 6,042,598 A | 3/2000 | Tsugita et al. |
| 6,059,825 A | 5/2000 | Hobbs et al. |
| 6,063,113 A | 5/2000 | Kavteladze et al. |
| 6,066,158 A | 5/2000 | Engelson et al. |
| 6,080,178 A | 6/2000 | Meglin |
| 6,093,196 A | 7/2000 | Okada |
| 6,093,199 A | 7/2000 | Brown et al. |
| 6,096,052 A | 8/2000 | Callister et al. |
| 6,099,549 A | 8/2000 | Bosma et al. |
| 6,117,154 A | 9/2000 | Barbut et al. |
| 6,123,715 A | 9/2000 | Amplatz |
| 6,126,673 A | 10/2000 | Kim et al. |
| 6,146,404 A | 11/2000 | Kim et al. |
| 6,152,946 A | 11/2000 | Broome et al. |
| 6,165,179 A | 12/2000 | Cathcart et al. |
| 6,165,198 A | 12/2000 | McGurk et al. |
| 6,168,579 B1 | 1/2001 | Tsugita |
| 6,168,603 B1 | 1/2001 | Leslie et al. |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,187,025 B1 | 2/2001 | Machek |
| 6,193,739 B1 | 2/2001 | Chevillon et al. |
| 6,214,025 B1 | 4/2001 | Thistle et al. |
| 6,217,600 B1 | 4/2001 | DiMatteo |
| 6,231,581 B1 | 5/2001 | Shank et al. |
| 6,231,589 B1 | 5/2001 | Wessman et al. |
| 6,235,044 B1 | 5/2001 | Root et al. |
| 6,235,045 B1 | 5/2001 | Barbut et al. |
| 6,241,746 B1 | 6/2001 | Bosma et al. |
| 6,245,012 B1 | 6/2001 | Kleshinski |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,901 B1 | 8/2001 | Whitcher et al. |
| 6,280,451 B1 | 8/2001 | Bates et al. |
| 6,280,457 B1 | 8/2001 | Wallace et al. |
| 6,290,721 B1 | 9/2001 | Heath |
| 6,328,755 B1 | 12/2001 | Marshall |
| 6,331,183 B1 | 12/2001 | Suon |
| 6,331,184 B1 | 12/2001 | Abrams |
| 6,342,062 B1 | 1/2002 | Suon et al. |
| 6,342,063 B1 | 1/2002 | Devries et al. |
| 6,344,041 B1 | 2/2002 | Kupiecki et al. |
| 6,355,051 B1 | 3/2002 | Sisskind et al. |
| 6,368,338 B1 | 4/2002 | Konya et al. |
| 6,383,205 B1 | 5/2002 | Samson et al. |
| 6,402,771 B1 | 6/2002 | Palmer et al. |
| 6,436,120 B1 | 8/2002 | Meglin |
| 6,436,121 B1 | 8/2002 | Blom |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,468,290 B1 | 10/2002 | Weldon et al. |
| 6,482,222 B1 | 11/2002 | Bruckheimer et al. |
| 6,506,205 B2 | 1/2003 | Goldberg et al. |
| 6,517,559 B1 | 2/2003 | O'Connell |
| 6,527,962 B1 | 3/2003 | Nadal |
| 6,537,294 B1 | 3/2003 | Boyle et al. |
| 6,540,767 B1 | 4/2003 | Walak et al. |
| 6,551,342 B1 | 4/2003 | Shen et al. |
| 6,562,058 B2 | 5/2003 | Seguin et al. |
| 6,589,265 B1 | 7/2003 | Palmer et al. |
| 6,599,307 B1 | 7/2003 | Huter et al. |
| 6,605,102 B1 | 8/2003 | Mazzocchi et al. |
| 6,652,558 B2 | 11/2003 | Patel et al. |
| 6,656,202 B2 | 12/2003 | Papp et al. |
| 6,660,021 B1 | 12/2003 | Palmer et al. |
| 6,695,878 B2 | 2/2004 | McGuckin et al. |
| 6,783,538 B2 | 8/2004 | McGuckin et al. |
| 6,793,665 B2 | 9/2004 | McGuckin et al. |
| 6,890,340 B2 | 5/2005 | Duane |
| 6,932,831 B2 | 8/2005 | Forber |
| 6,958,074 B2 | 10/2005 | Russell |
| 6,972,025 B2 | 12/2005 | WasDyke |
| 6,989,021 B2 * | 1/2006 | Bosma et al. ................ 606/200 |
| 6,994,092 B2 | 2/2006 | van der Burg et al. |
| 7,011,094 B2 | 3/2006 | Rapacki et al. |
| 7,037,321 B2 | 5/2006 | Sachdeva et al. |
| 7,097,651 B2 | 8/2006 | Harrison et al. |
| 7,232,462 B2 | 6/2007 | Schaeffer et al. |
| 7,279,000 B2 | 10/2007 | Cartier et al. |
| 7,316,708 B2 | 1/2008 | Gordon et al. |
| 7,323,003 B2 | 1/2008 | Lowe |
| 7,338,512 B2 | 3/2008 | McGuckin, Jr. et al. |
| 7,534,251 B2 | 5/2009 | WasDyke |
| 7,572,289 B2 * | 8/2009 | Sisken et al. ................ 623/1.36 |
| 7,704,266 B2 * | 4/2010 | Thinnes et al. ............... 606/200 |
| 7,867,245 B2 | 1/2011 | Neeman et al. |
| 7,875,018 B2 | 1/2011 | Tockman et al. |

(56) References Cited

U.S. PATENT DOCUMENTS

| | | |
|---|---|---|
| 8,029,529 B1 | 10/2011 | Chanduszko |
| 2002/0058911 A1 | 5/2002 | Gilson et al. |
| 2002/0116024 A1 | 8/2002 | Goldberg et al. |
| 2002/0193827 A1 | 12/2002 | McGuckin et al. |
| 2002/0193828 A1 | 12/2002 | Griffin et al. |
| 2003/0130680 A1 | 7/2003 | Russell |
| 2003/0195555 A1 | 10/2003 | Khairkhahan et al. |
| 2003/0208227 A1 | 11/2003 | Thomas |
| 2003/0208253 A1 | 11/2003 | Beyer et al. |
| 2004/0044361 A1 | 3/2004 | Frazier et al. |
| 2004/0073252 A1 | 4/2004 | Goldberg et al. |
| 2004/0093017 A1 | 5/2004 | Chanduszko |
| 2004/0158273 A1 | 8/2004 | Weaver et al. |
| 2004/0186510 A1 | 9/2004 | Weaver |
| 2004/0186556 A1 | 9/2004 | Hogendijk et al. |
| 2004/0215230 A1 | 10/2004 | Frazier et al. |
| 2004/0230220 A1 | 11/2004 | Osborne |
| 2005/0004596 A1 | 1/2005 | McGuckin et al. |
| 2005/0015111 A1 | 1/2005 | McGuckin et al. |
| 2005/0027314 A1 | 2/2005 | WasDyke |
| 2005/0043757 A1 | 2/2005 | Arad et al. |
| 2005/0165442 A1 | 7/2005 | Thinnes, Jr. et al. |
| 2005/0182439 A1 | 8/2005 | Lowe |
| 2005/0234503 A1 | 10/2005 | Ravenscroft et al. |
| 2005/0251199 A1 | 11/2005 | Osborne et al. |
| 2005/0267514 A1 | 12/2005 | Osborne et al. |
| 2005/0267515 A1* | 12/2005 | Oliva et al. .................. 606/200 |
| 2005/0277977 A1 | 12/2005 | Thornton |
| 2005/0288704 A1 | 12/2005 | Cartier et al. |
| 2006/0030875 A1 | 2/2006 | Tessmer |
| 2006/0058832 A1 | 3/2006 | Melzer et al. |
| 2006/0079928 A1 | 4/2006 | Cartier et al. |
| 2006/0079930 A1 | 4/2006 | McGuckin et al. |
| 2006/0095068 A1 | 5/2006 | WasDyke et al. |
| 2006/0100660 A1 | 5/2006 | Osborne et al. |
| 2006/0106417 A1 | 5/2006 | Tessmer et al. |
| 2006/0149295 A1 | 7/2006 | Fleming, III |
| 2006/0178695 A1 | 8/2006 | Decant et al. |
| 2006/0206138 A1 | 9/2006 | Eidenschink |
| 2007/0005095 A1 | 1/2007 | Osborne et al. |
| 2007/0032816 A1 | 2/2007 | O'Connell et al. |
| 2007/0088381 A1 | 4/2007 | McGuckin et al. |
| 2007/0173885 A1 | 7/2007 | Cartier et al. |
| 2008/0188887 A1 | 8/2008 | Batiste |
| 2008/0221609 A1 | 9/2008 | McGuckin et al. |
| 2008/0275486 A1 | 11/2008 | Dwyer et al. |
| 2009/0198270 A1 | 8/2009 | McGuckin et al. |
| 2010/0049238 A1 | 2/2010 | Simpson |
| 2010/0049239 A1 | 2/2010 | McGuckin et al. |
| 2010/0106178 A1 | 4/2010 | Obermiller et al. |

FOREIGN PATENT DOCUMENTS

| | | |
|---|---|---|
| EP | 1880693 | 1/2008 |
| FR | 2567405 | 1/1986 |
| WO | 9312723 | 7/1993 |
| WO | WO-93/12723 | 7/1993 |
| WO | 9509567 | 4/1995 |
| WO | WO-95/09567 | 4/1995 |
| WO | 9925252 | 5/1999 |
| WO | WO-99/25252 | 5/1999 |
| WO | 0145590 | 6/2001 |
| WO | WO-01/45590 | 6/2001 |
| WO | 0162184 | 8/2001 |
| WO | WO-01/62184 | 8/2001 |
| WO | 0172239 | 10/2001 |
| WO | WO-01/72239 | 10/2001 |
| WO | 02/11812 | 2/2002 |
| WO | 0211812 | 2/2002 |
| WO | WO 0232496 | 4/2002 |
| WO | WO-02/102436 | 12/2002 |
| WO | 03063732 | 8/2003 |
| WO | WO-03/063732 | 8/2003 |
| WO | 2004049973 | 6/2004 |
| WO | WO-2004/049973 | 6/2004 |
| WO | 2005034764 | 4/2005 |
| WO | WO-2005/034764 | 4/2005 |
| WO | 2005/117750 | 12/2005 |
| WO | 2006/036457 | 4/2006 |

OTHER PUBLICATIONS

Gianturco-Roehm, Bird's Nest® Vena Cava Filter.
Cordis Corporation, TrapEase™ Permanent Vena Cava Filter. "A Small, Easy and Versatile System for Optimal Pulmonary Emboli Prevention", 2000 (4 pages).

* cited by examiner

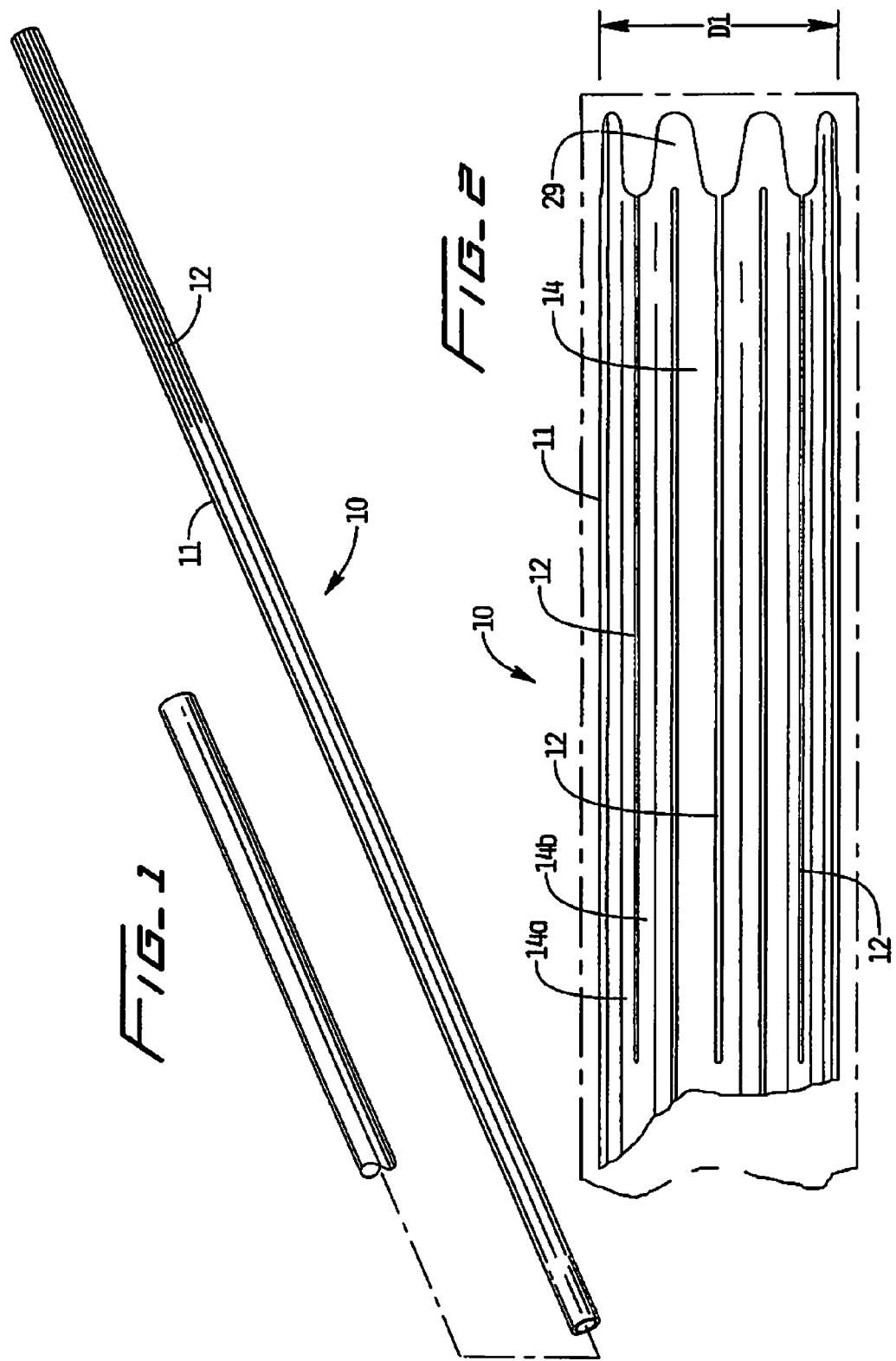

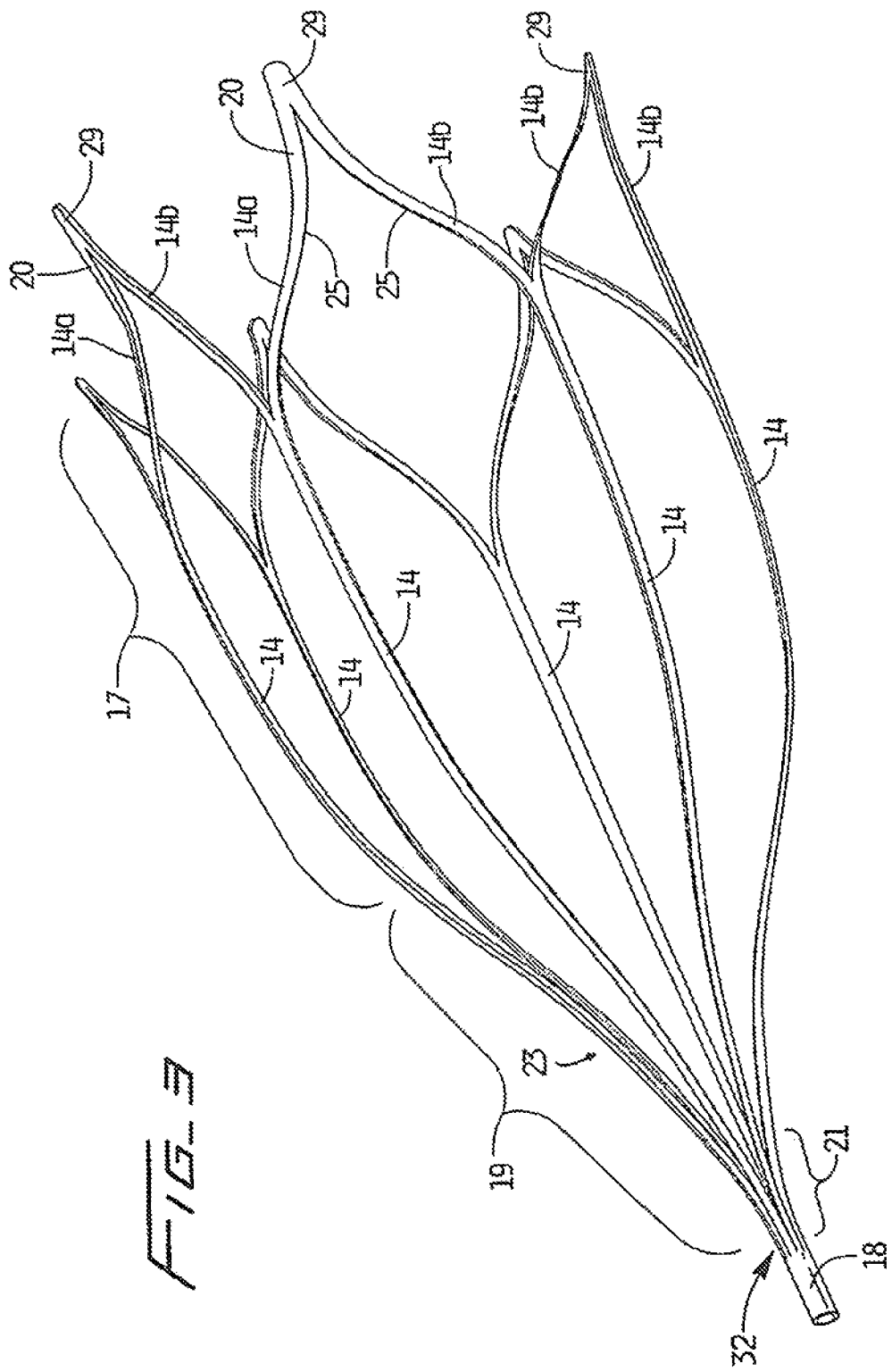

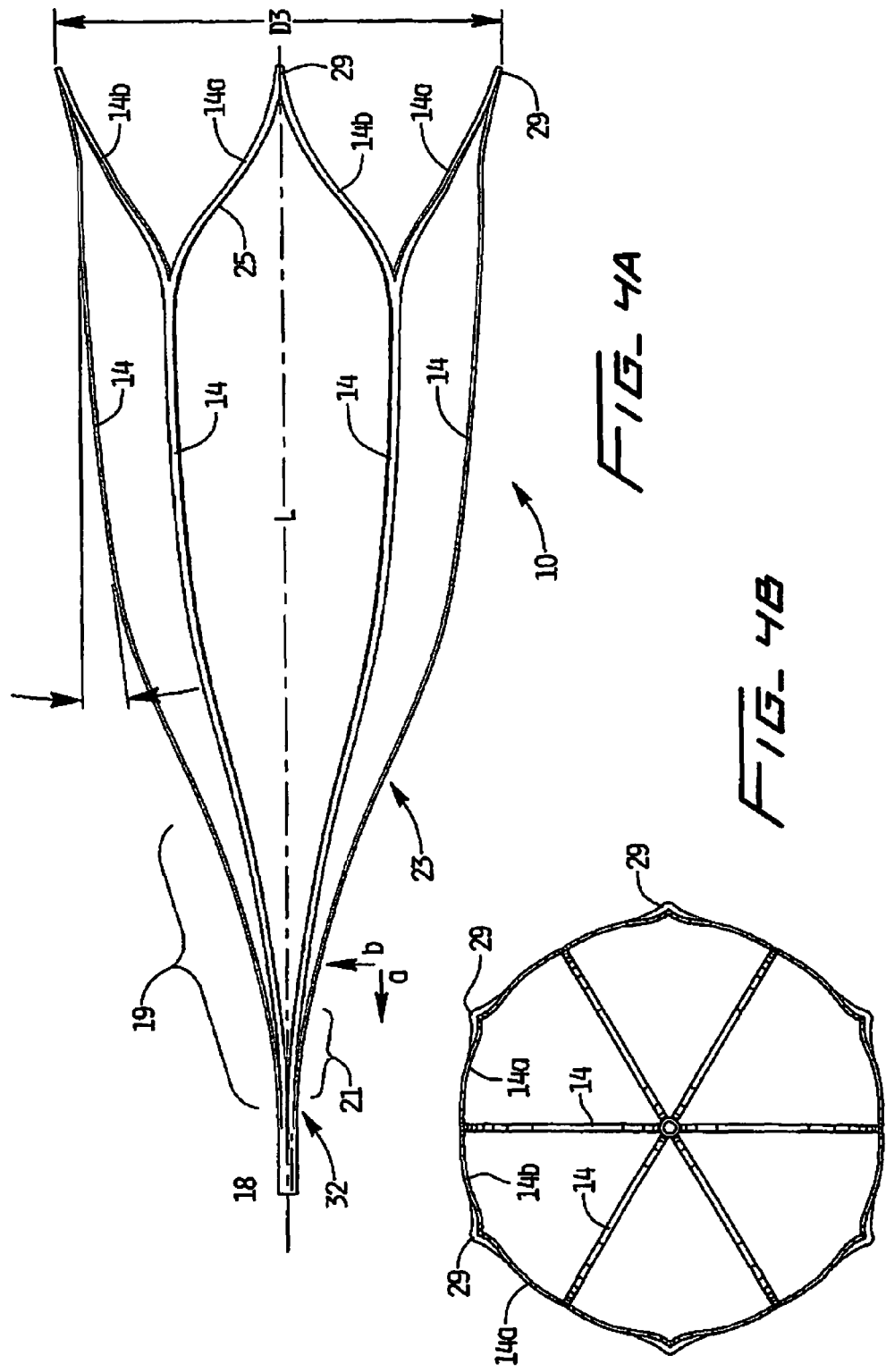

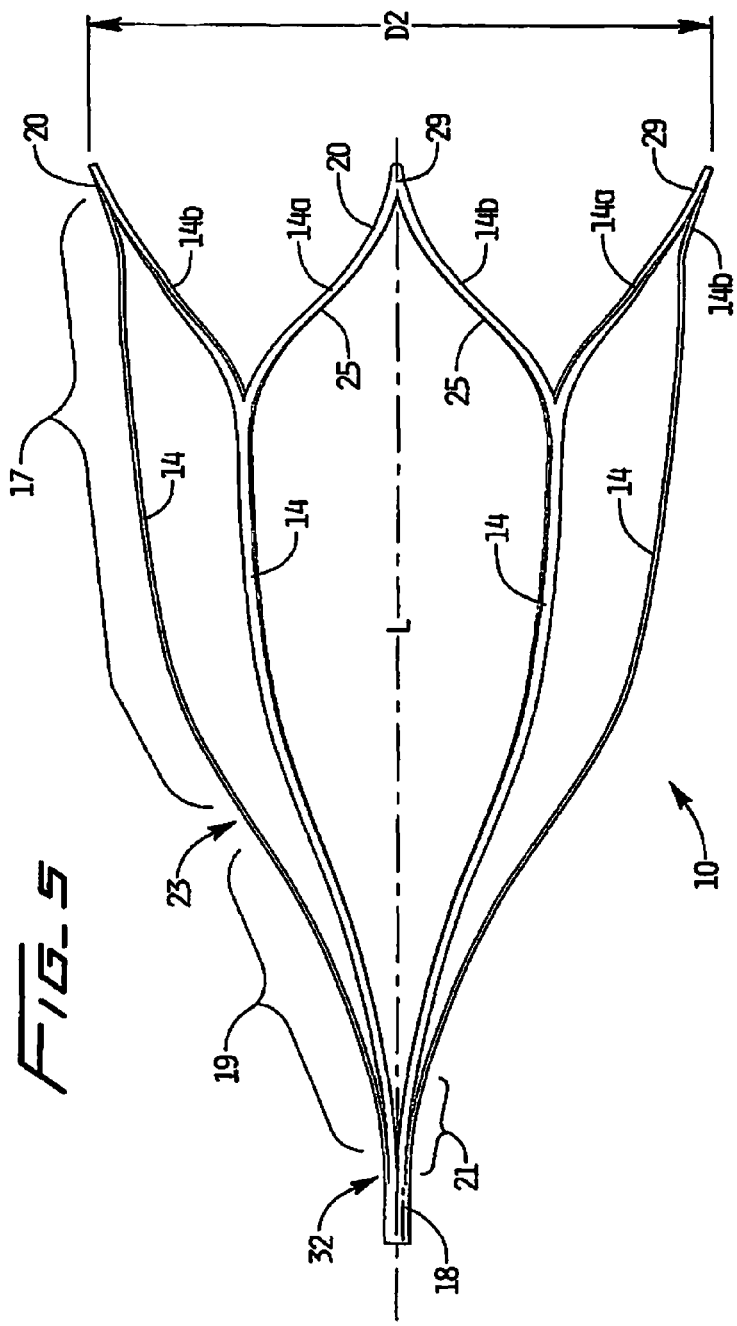

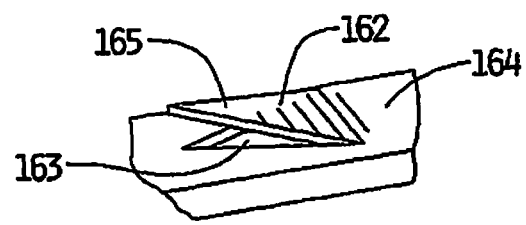
FIG_6A
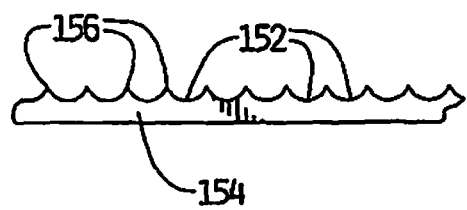
FIG_6B

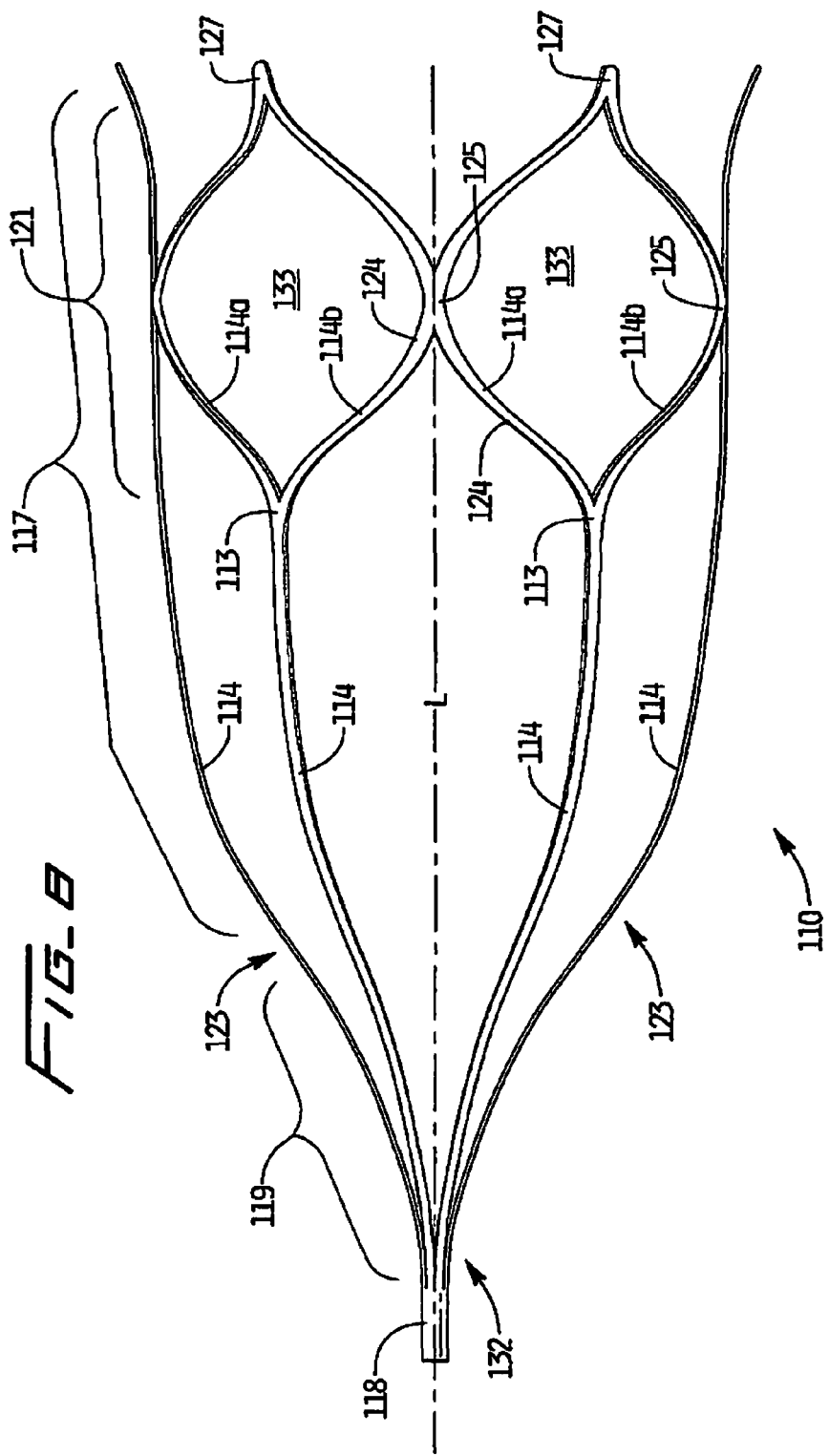

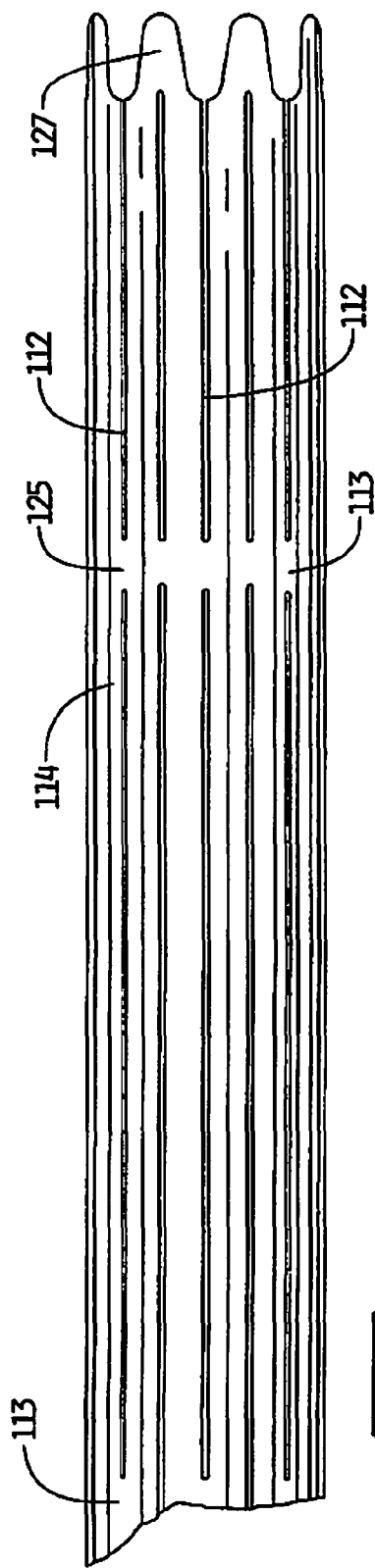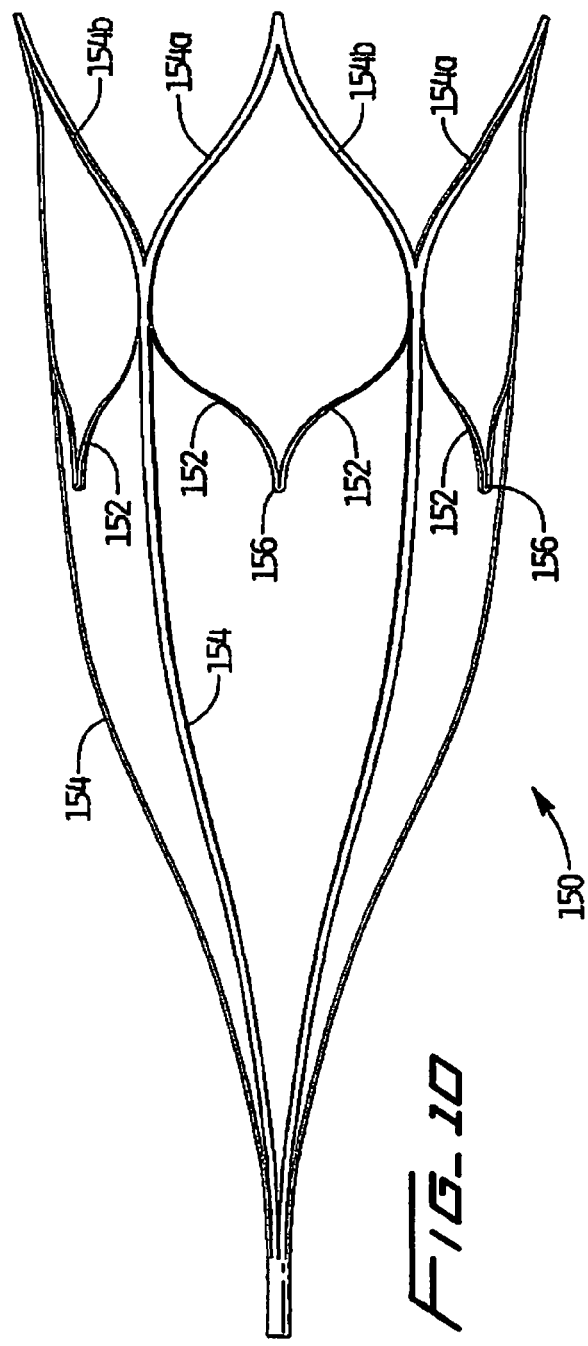

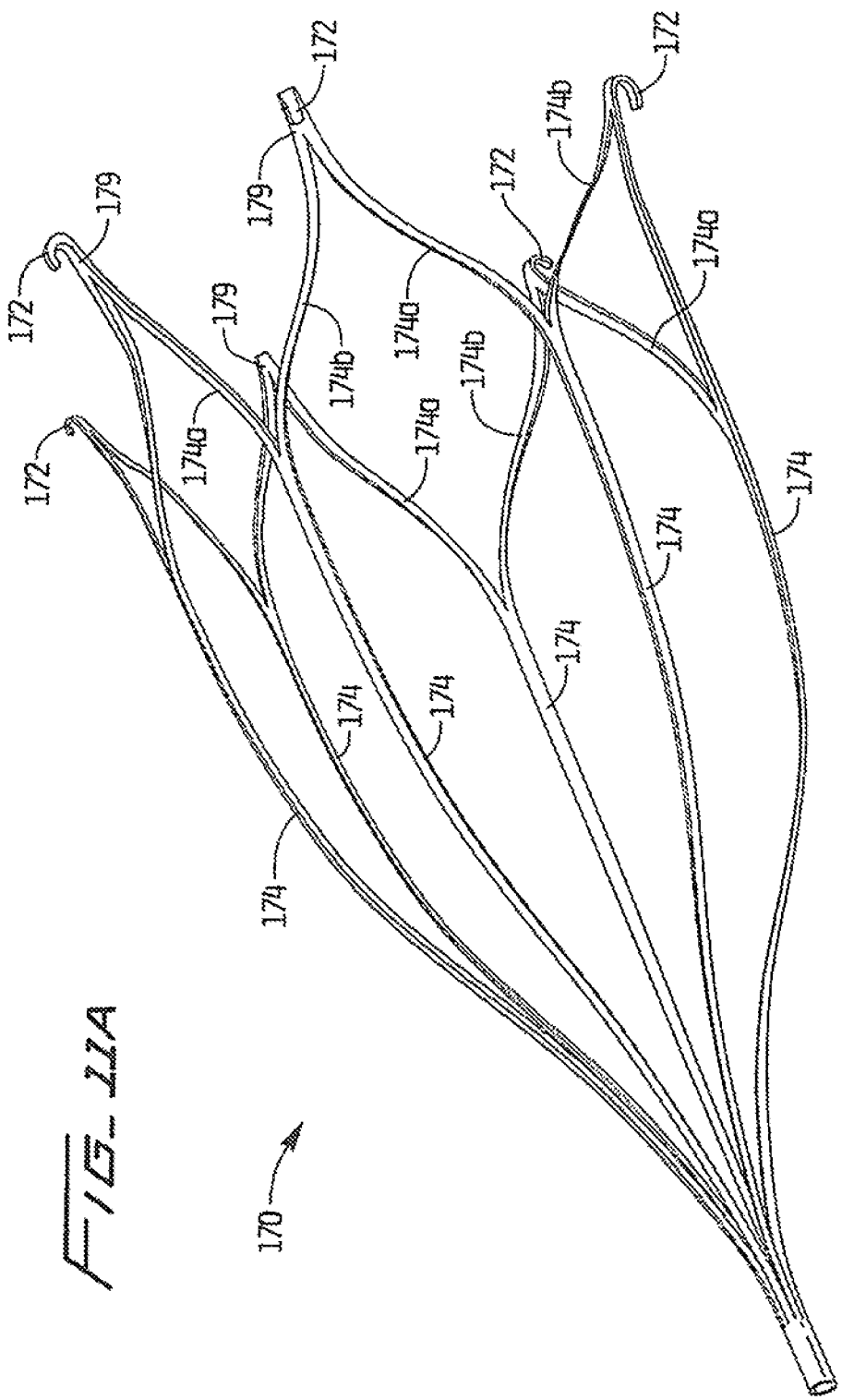

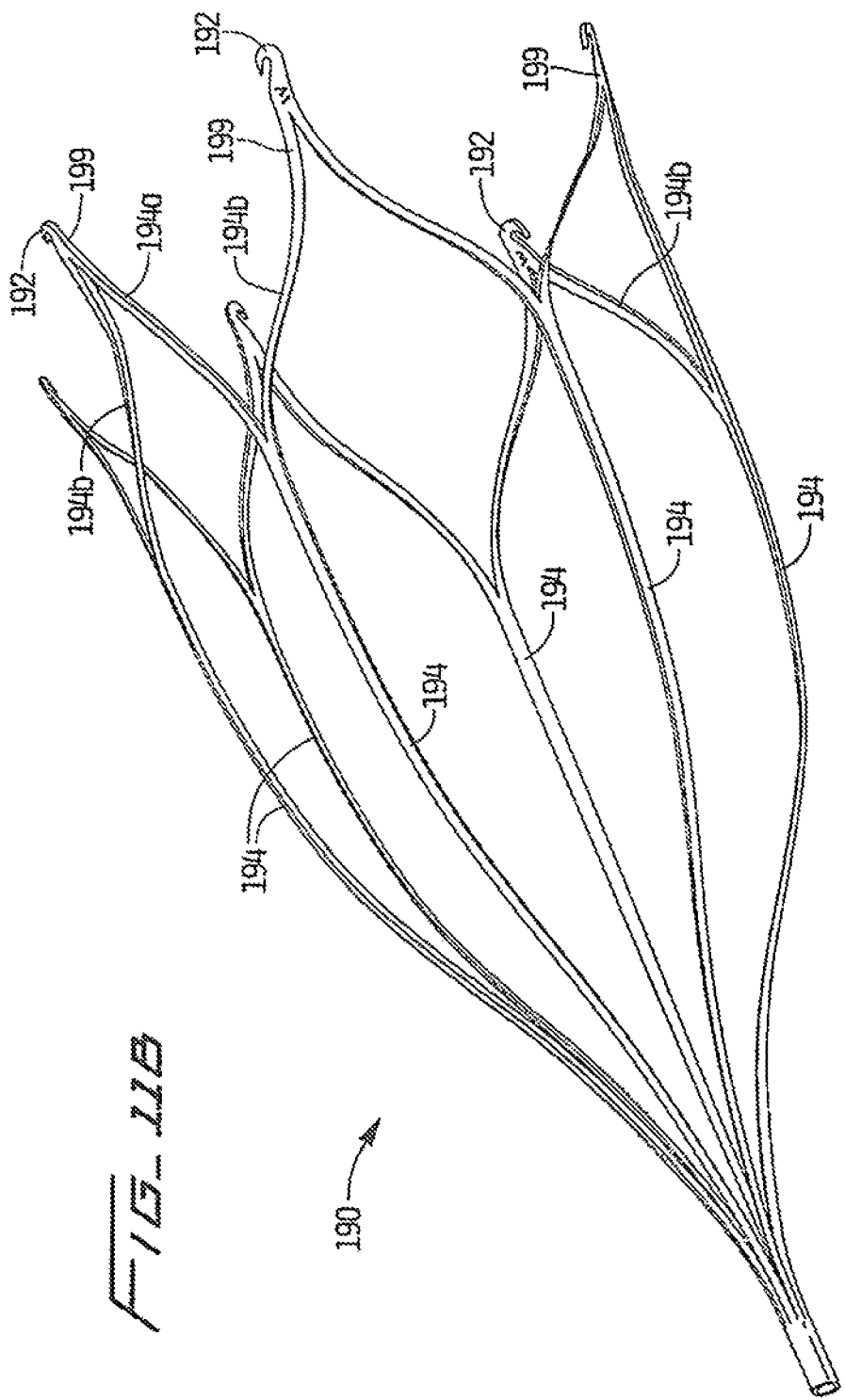

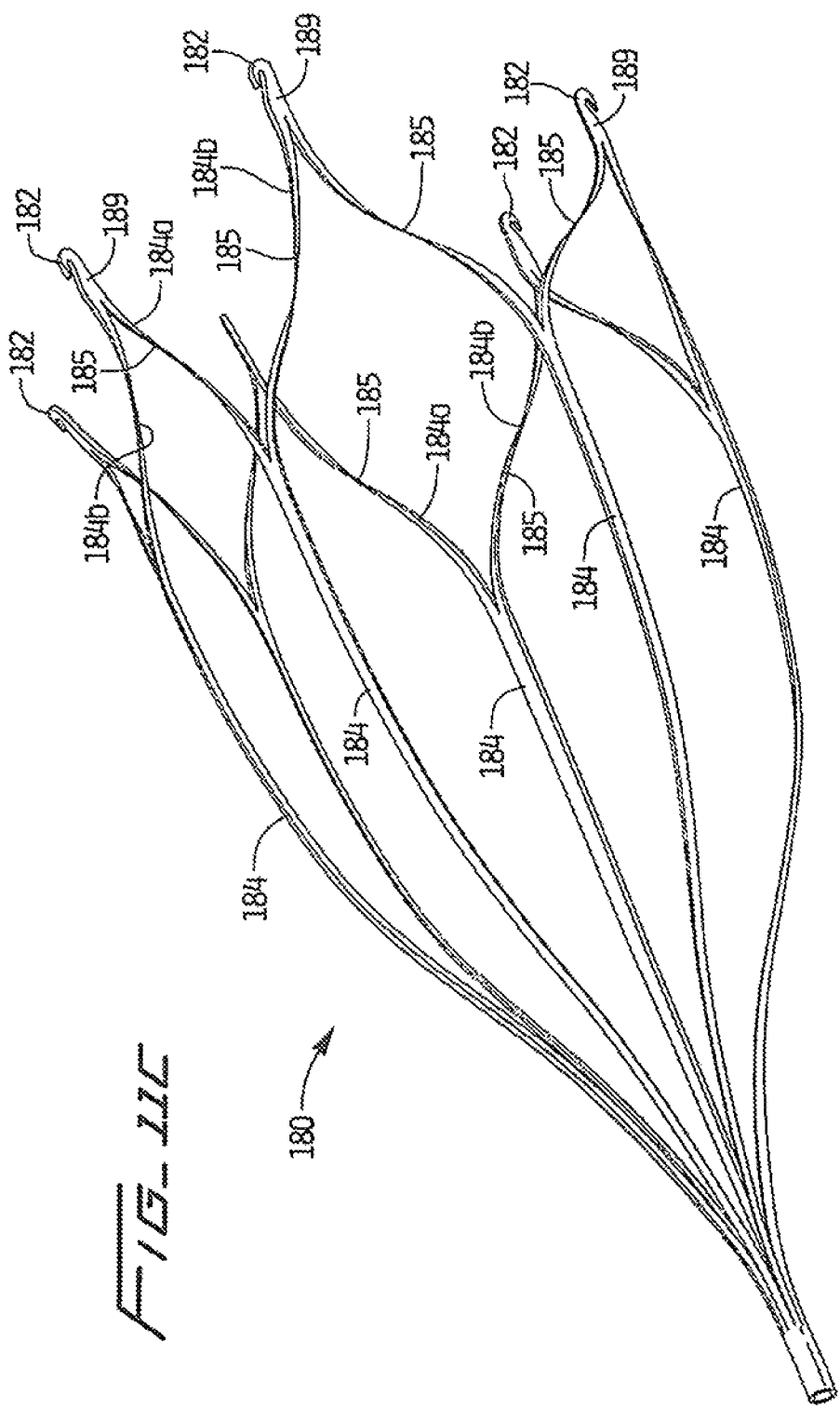

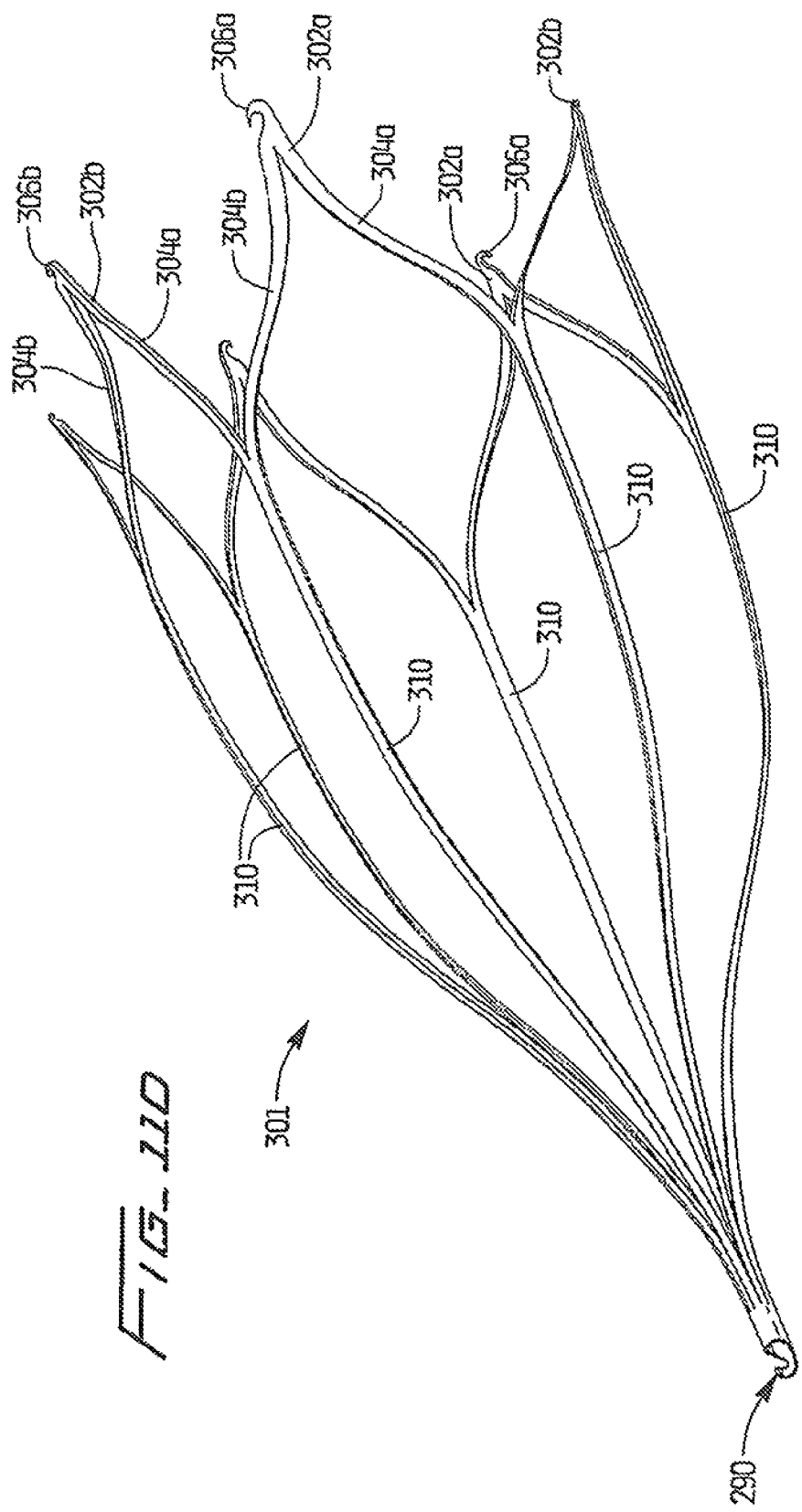

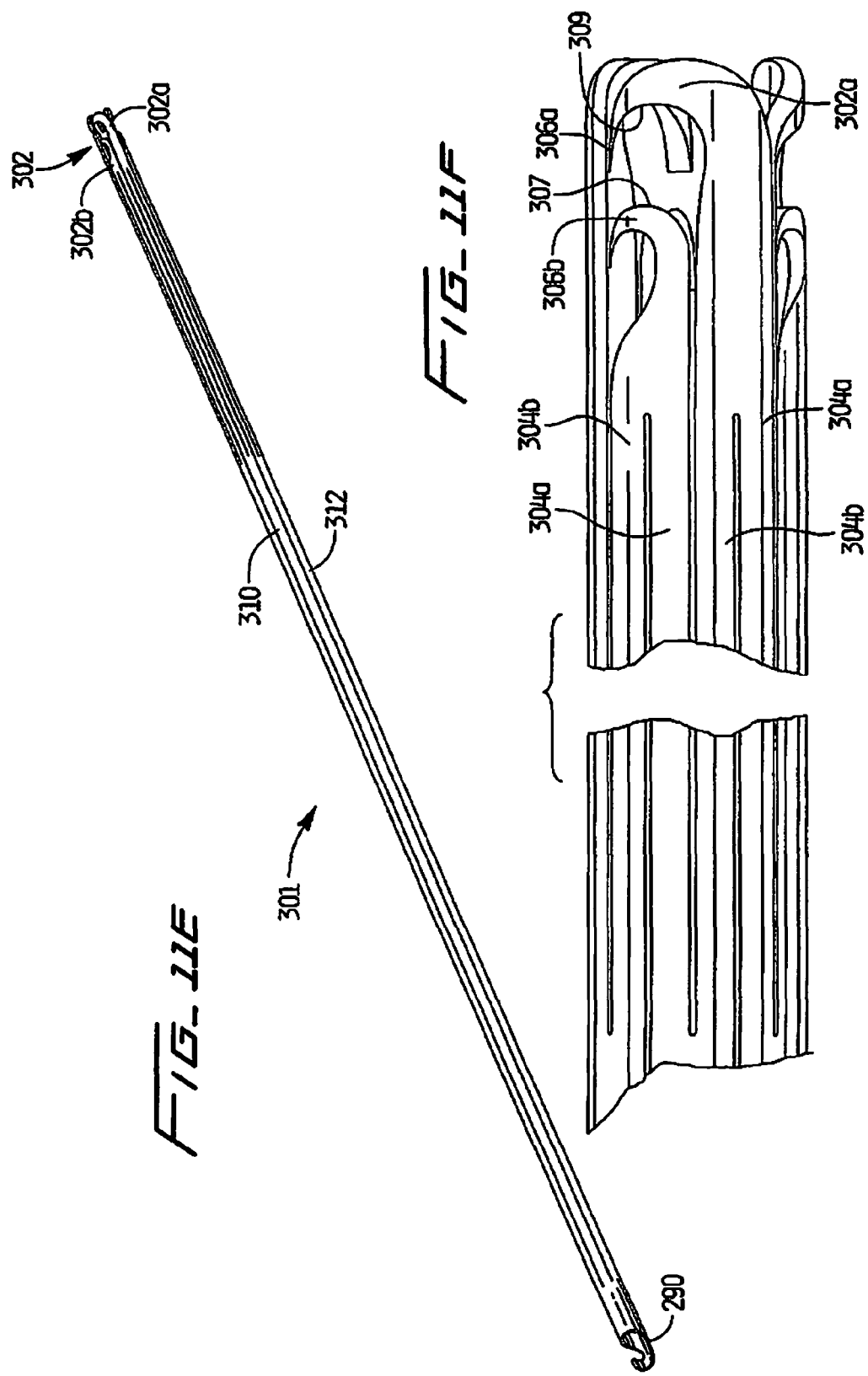

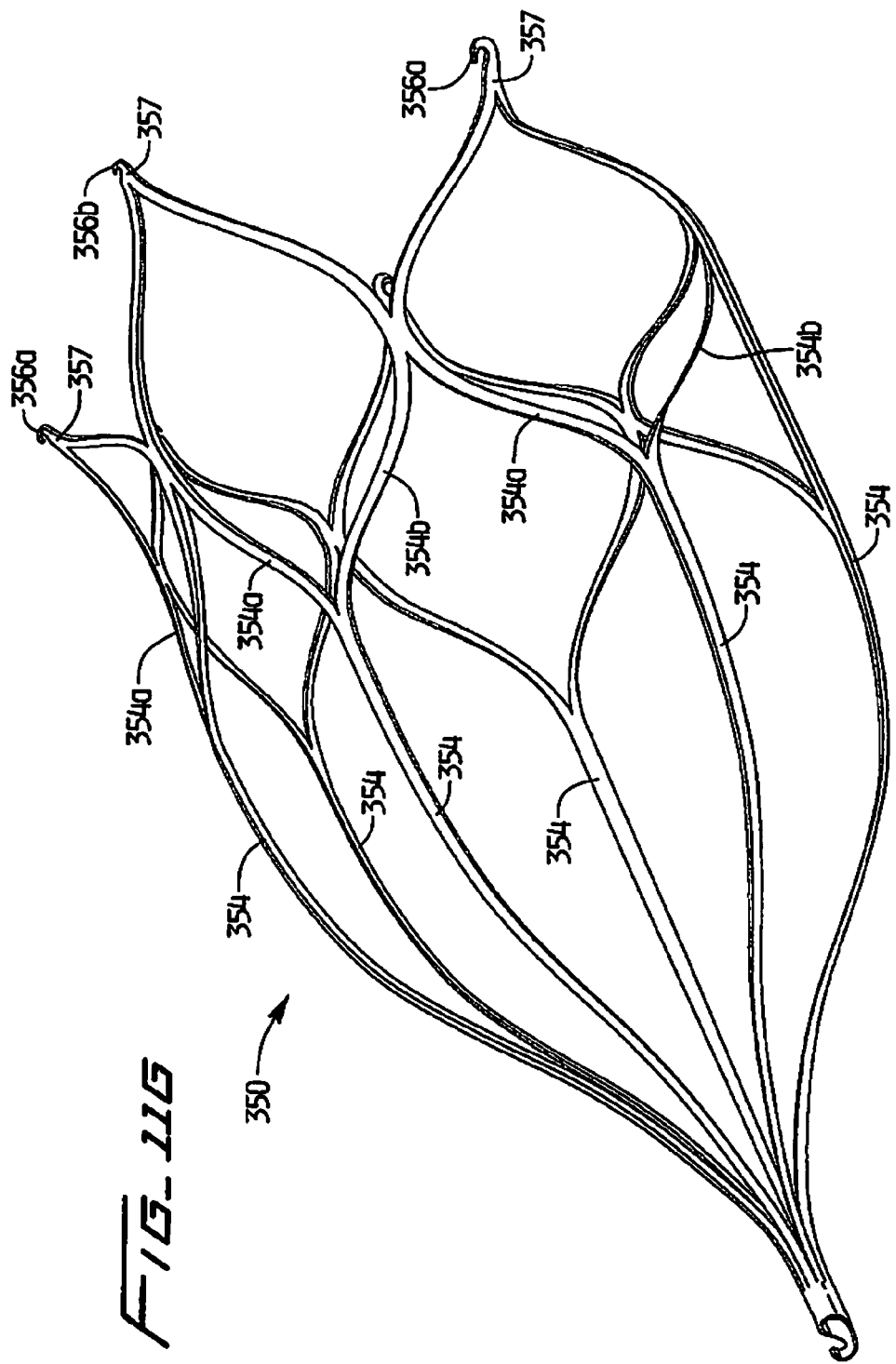

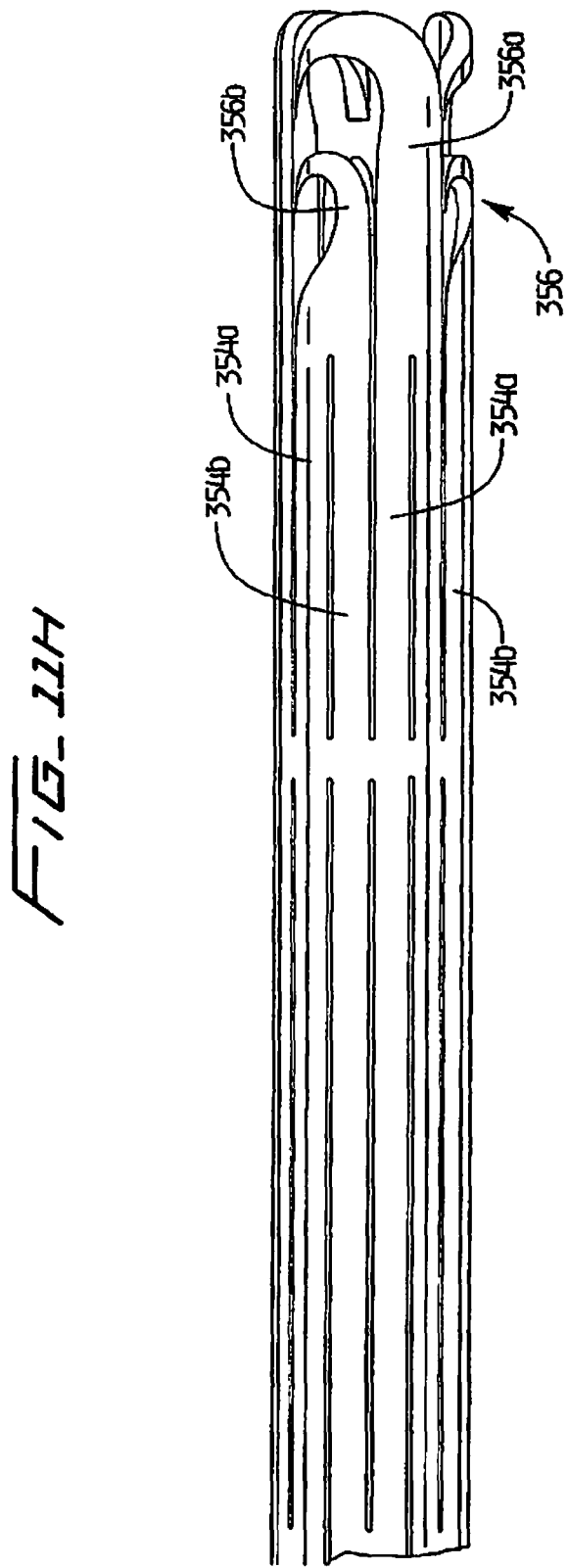

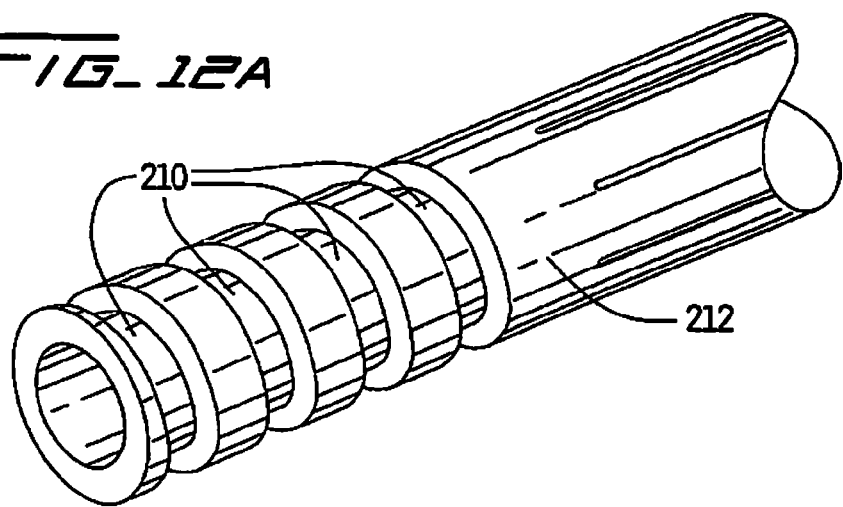
FIG_12A
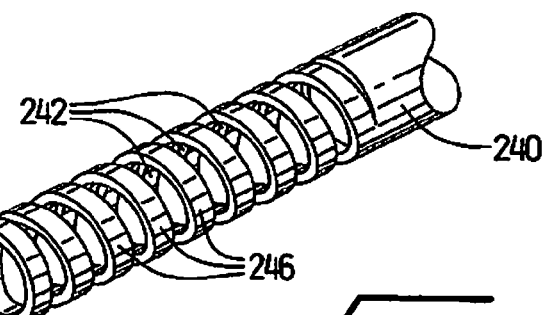
FIG_12B
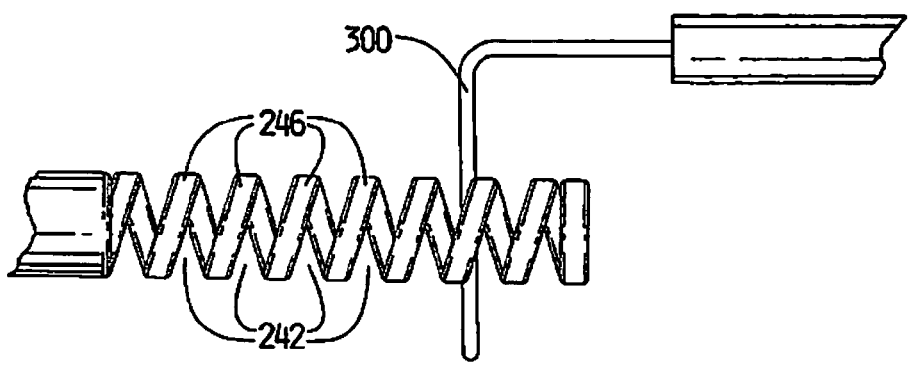
FIG_12C

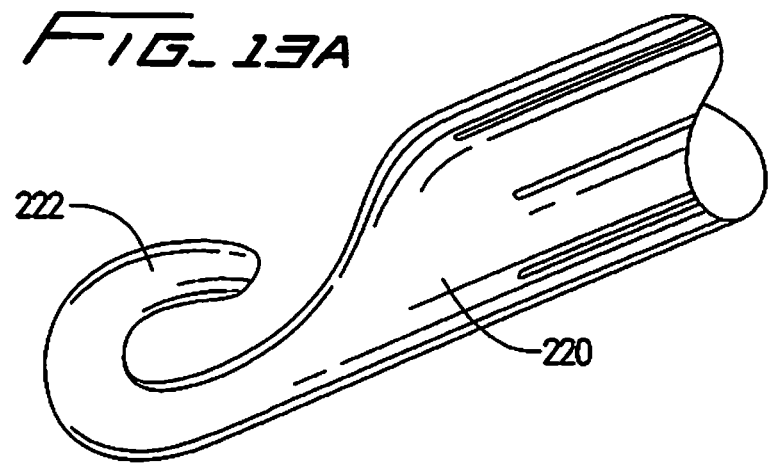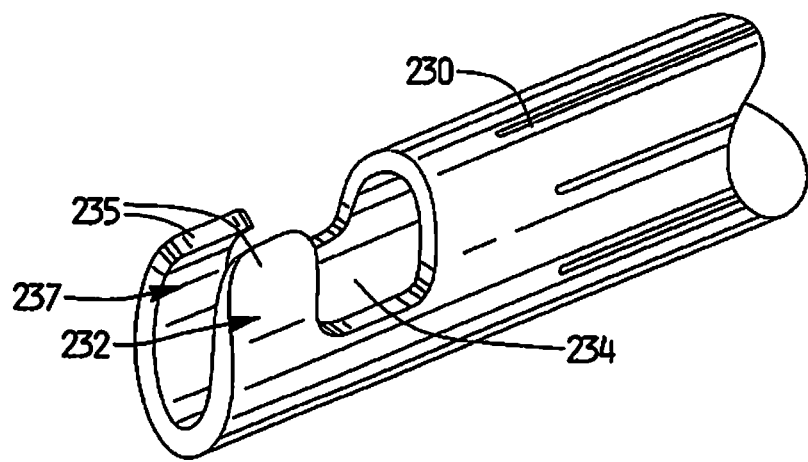

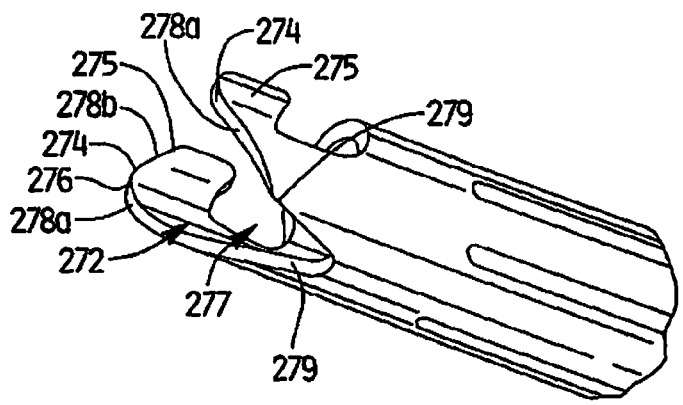
FIG_13C
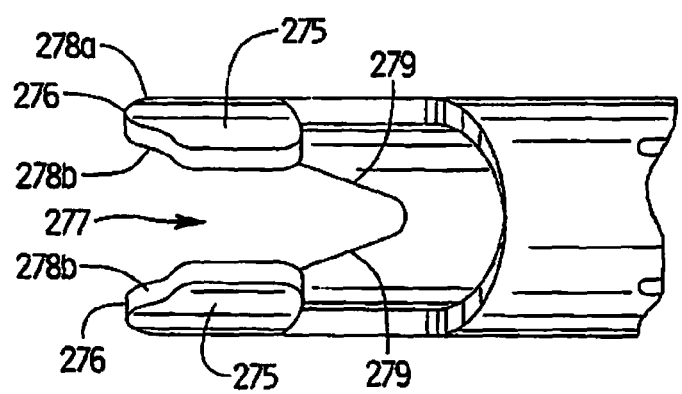
FIG_13D
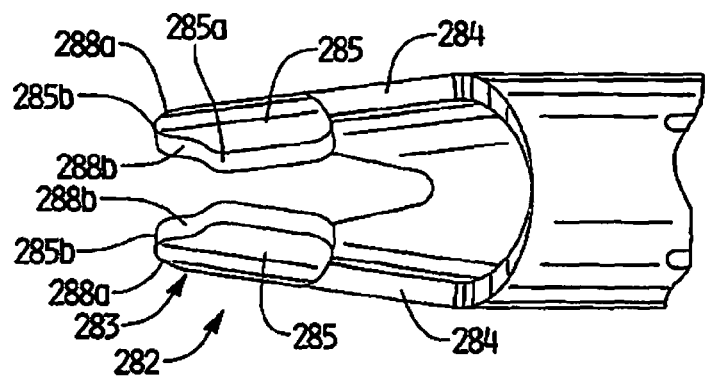
FIG_13E

FIG_13F
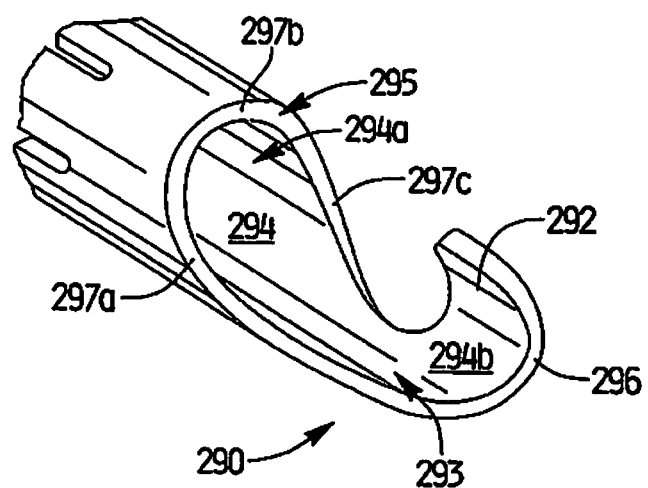
FIG_13G
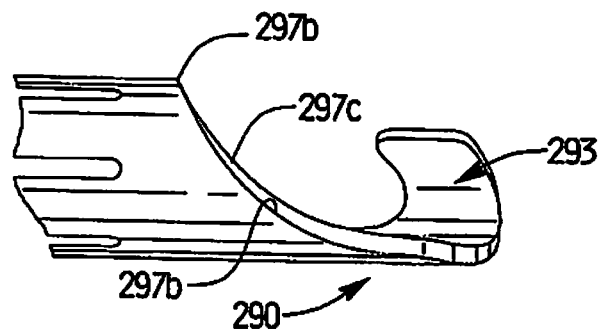

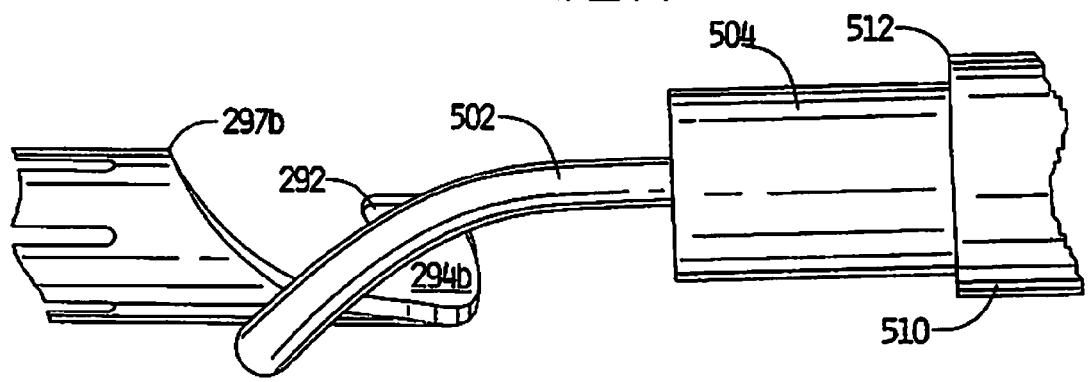
FIG_13H
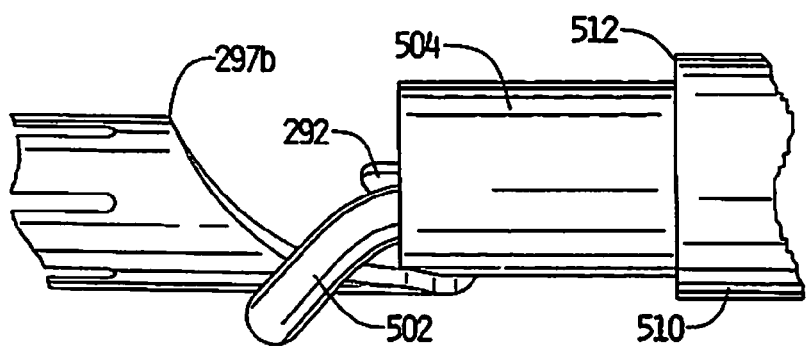
FIG_13I
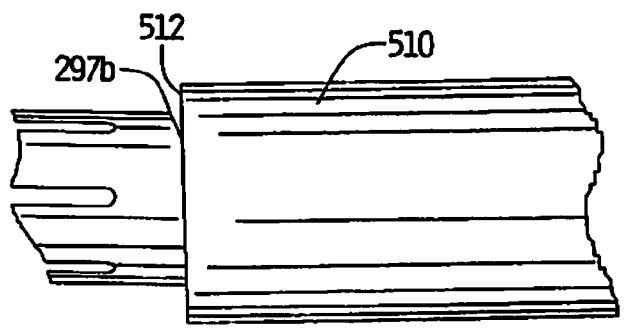
FIG_13J

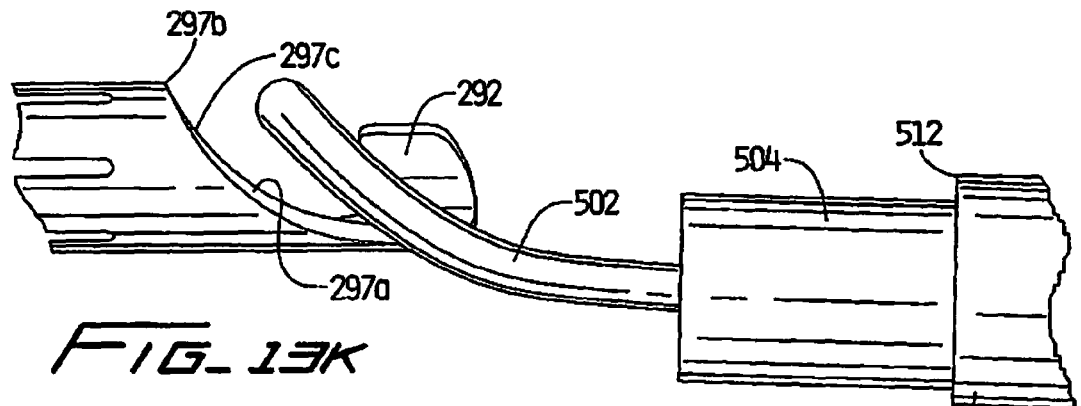
FIG_13K
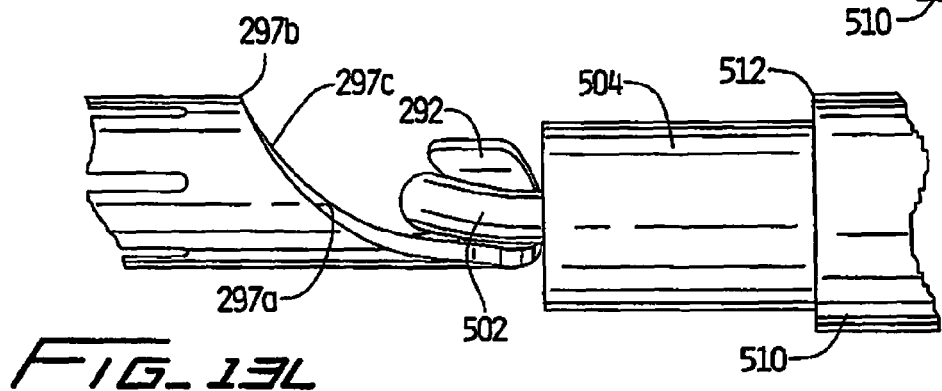
FIG_13L
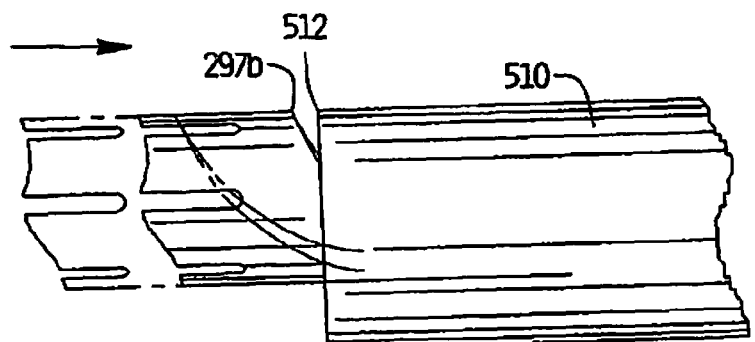
FIG_13M
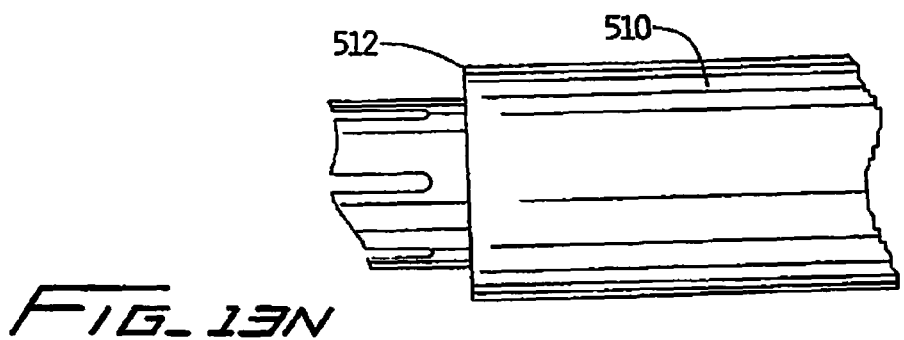
FIG_13N

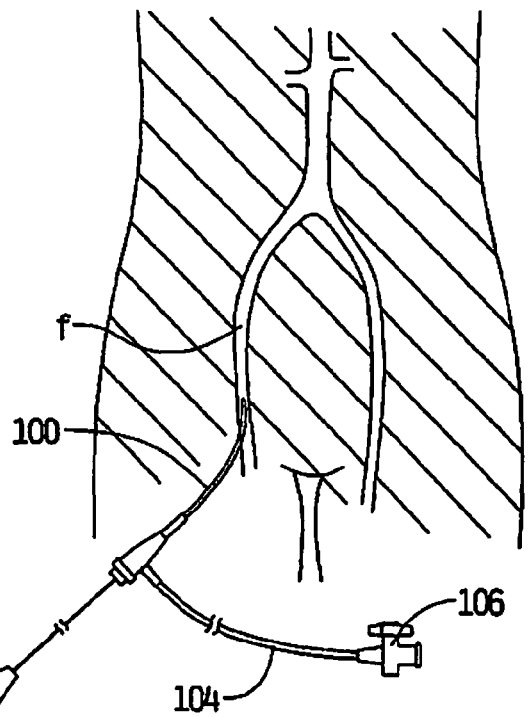
FIG_14
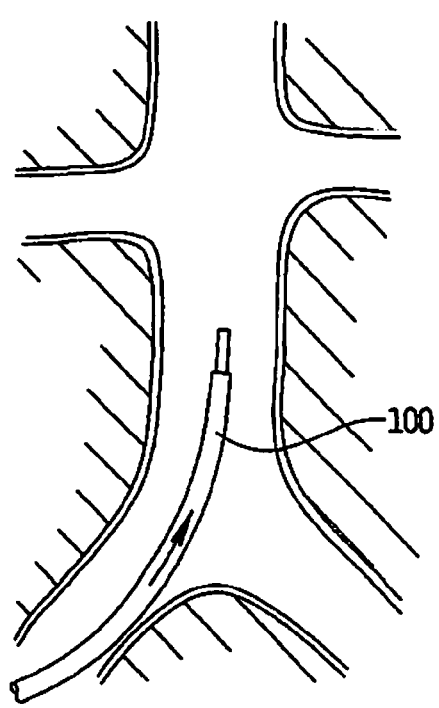
FIG_15
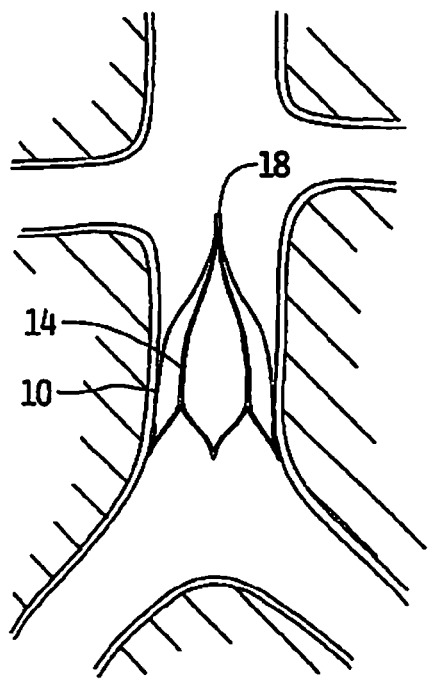
FIG_16

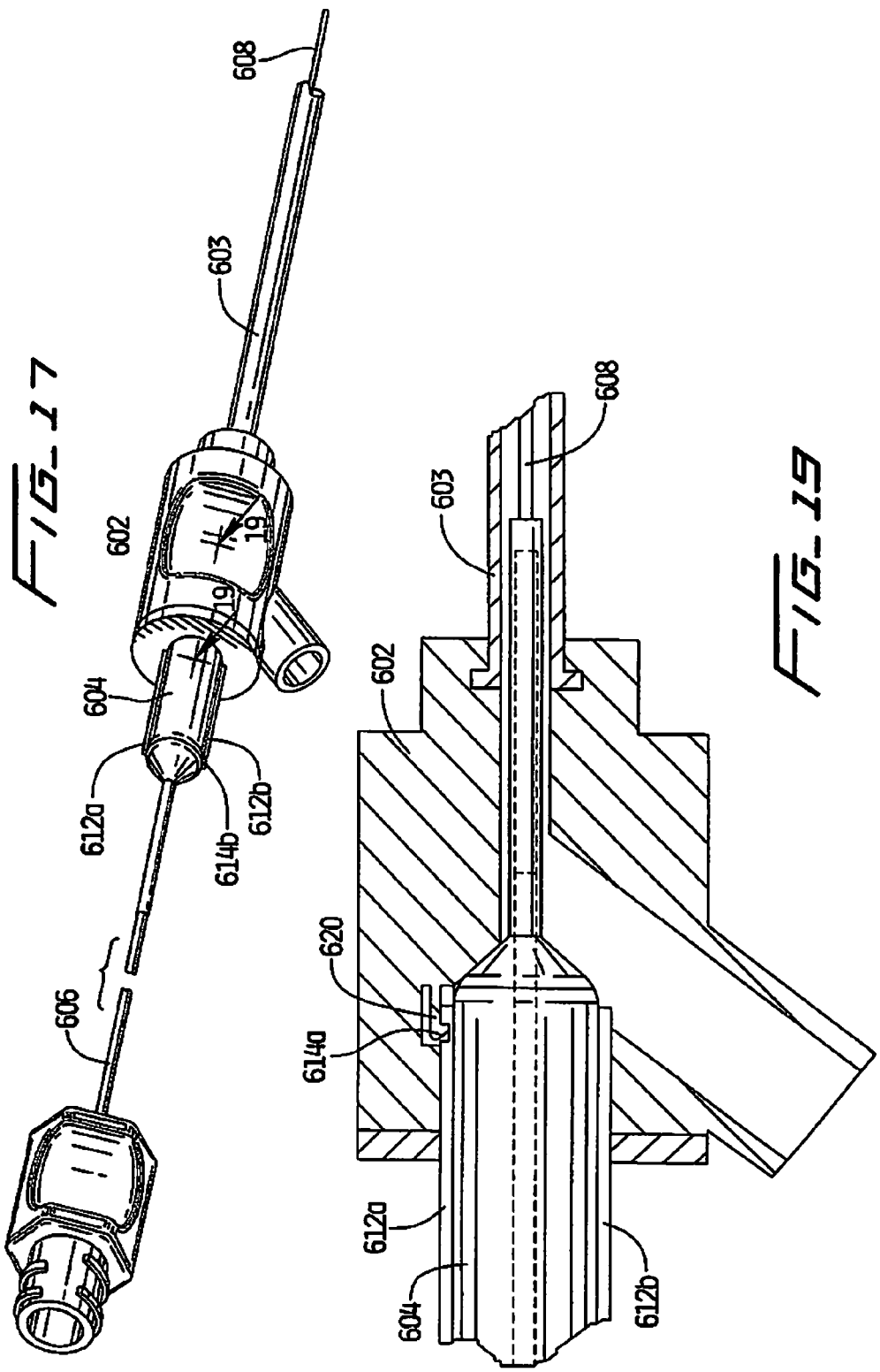

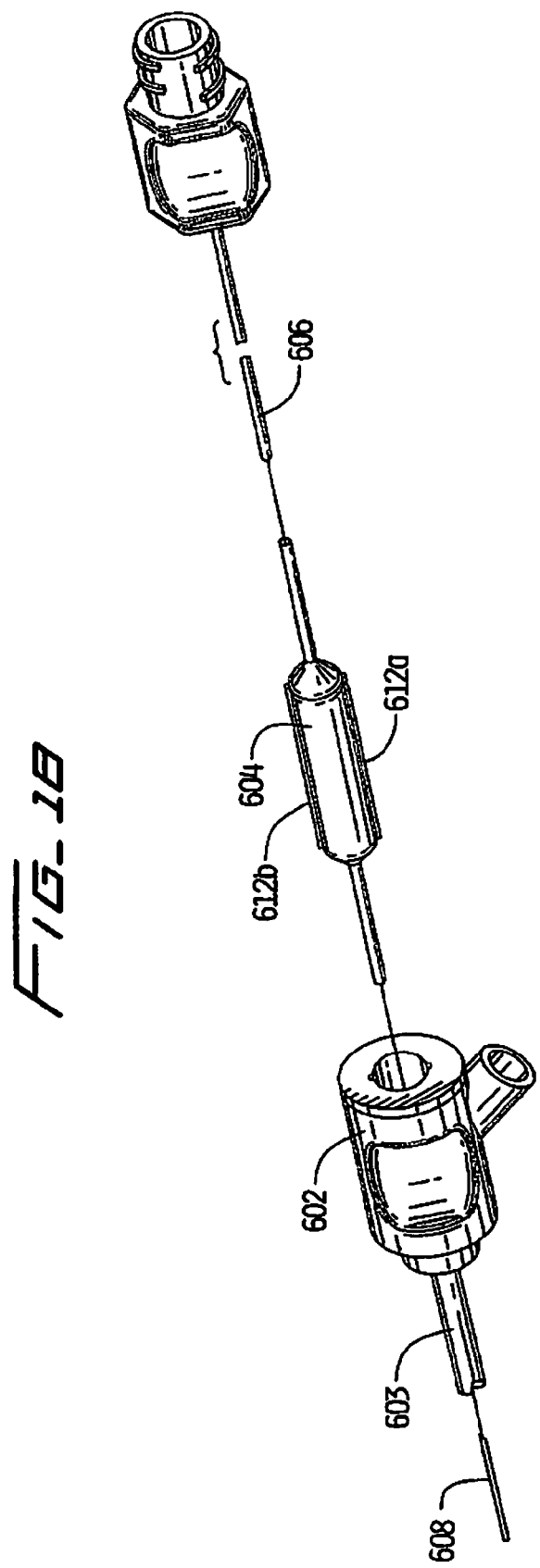

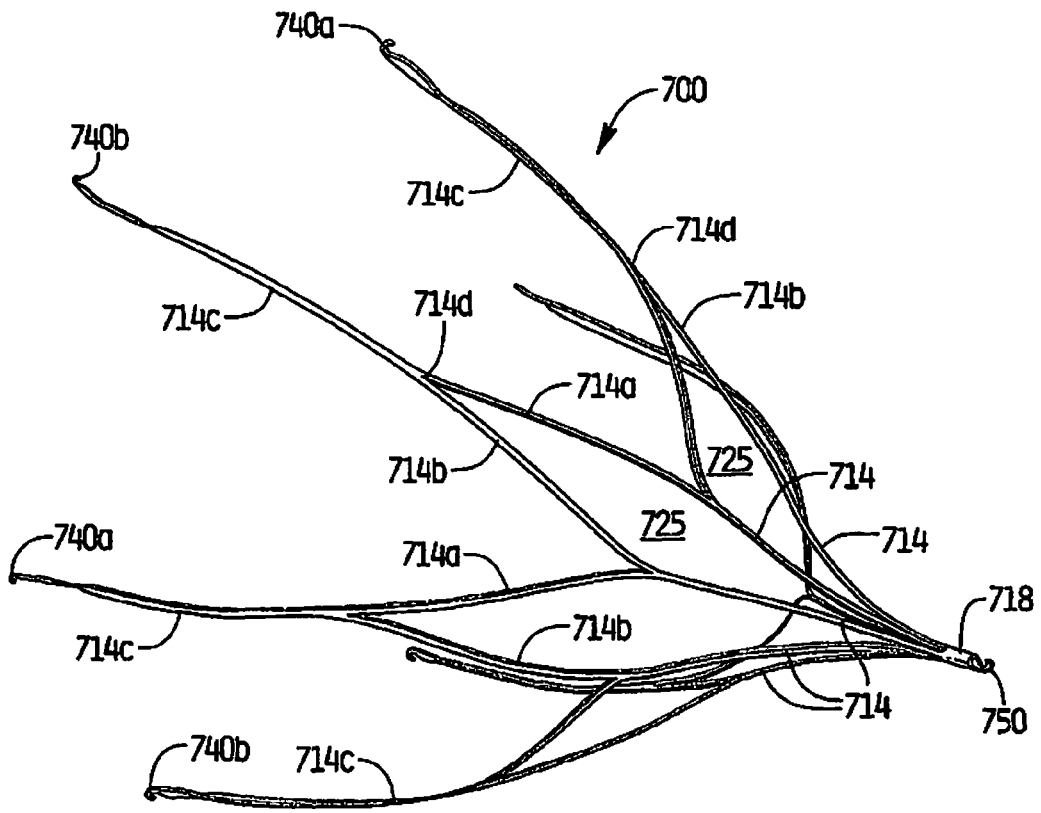
FIG_20A
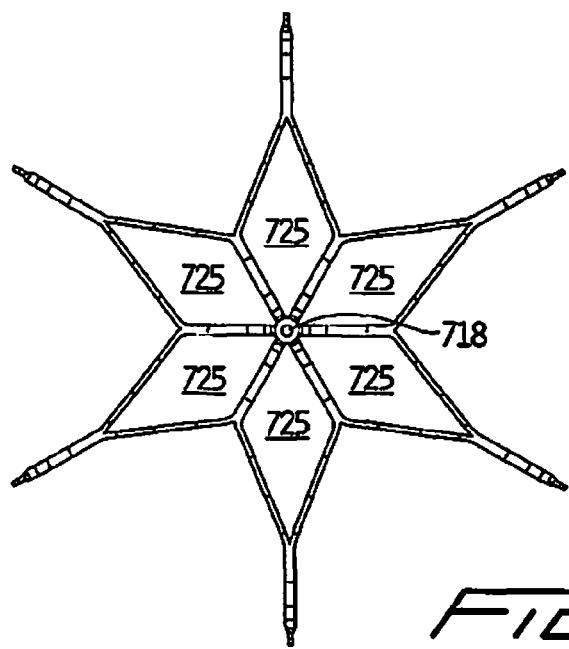
FIG_20B

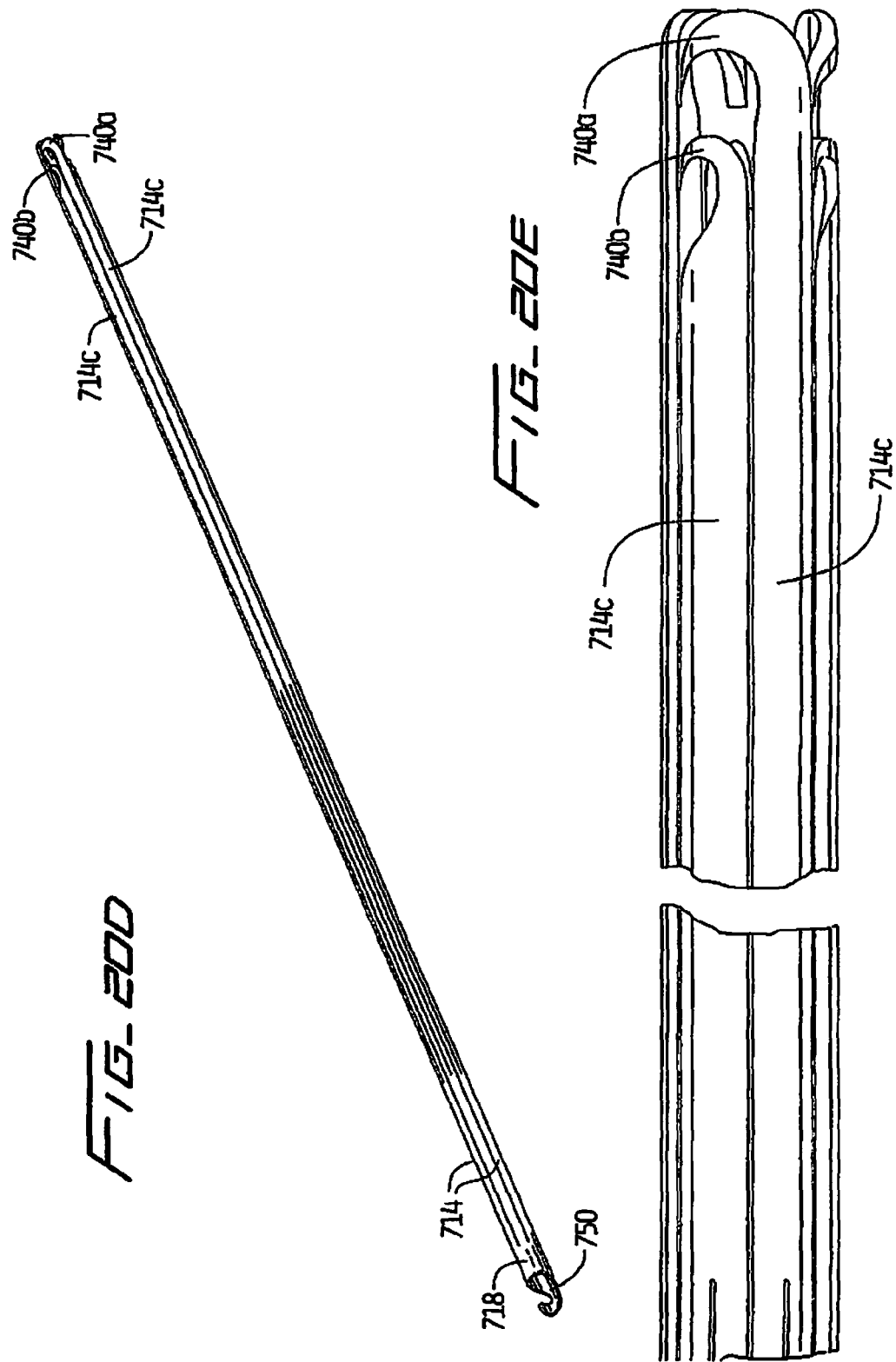

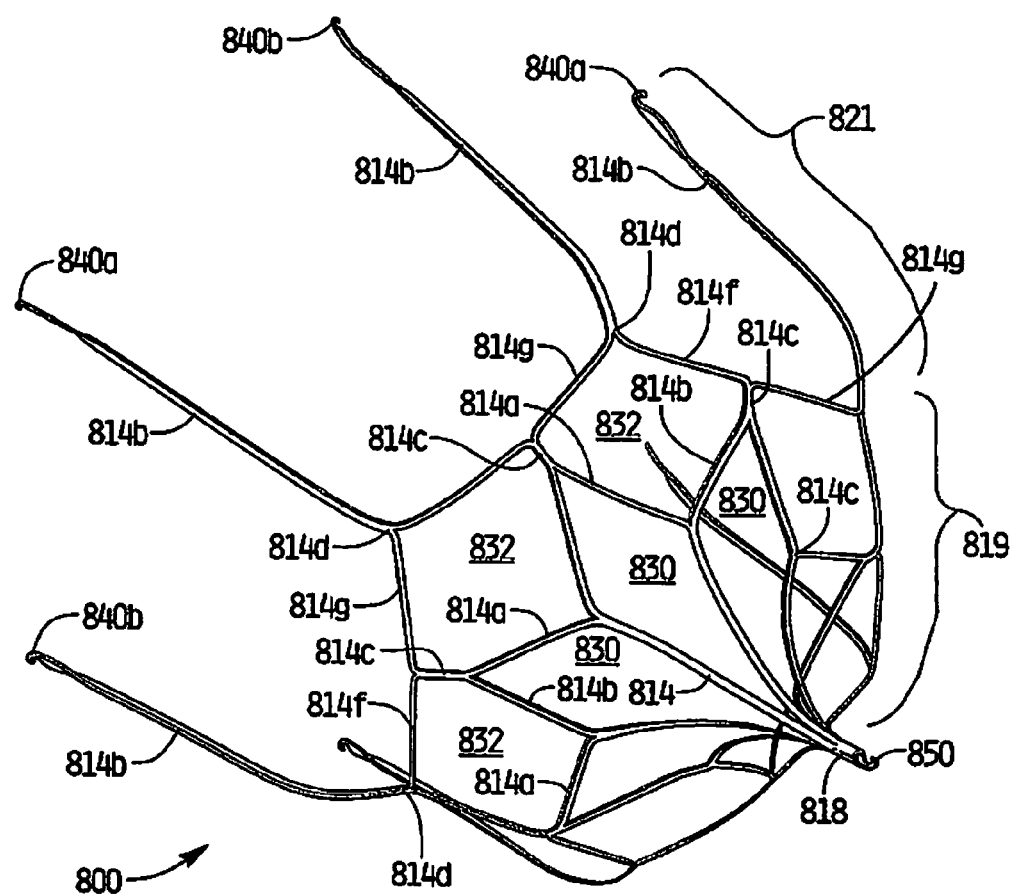

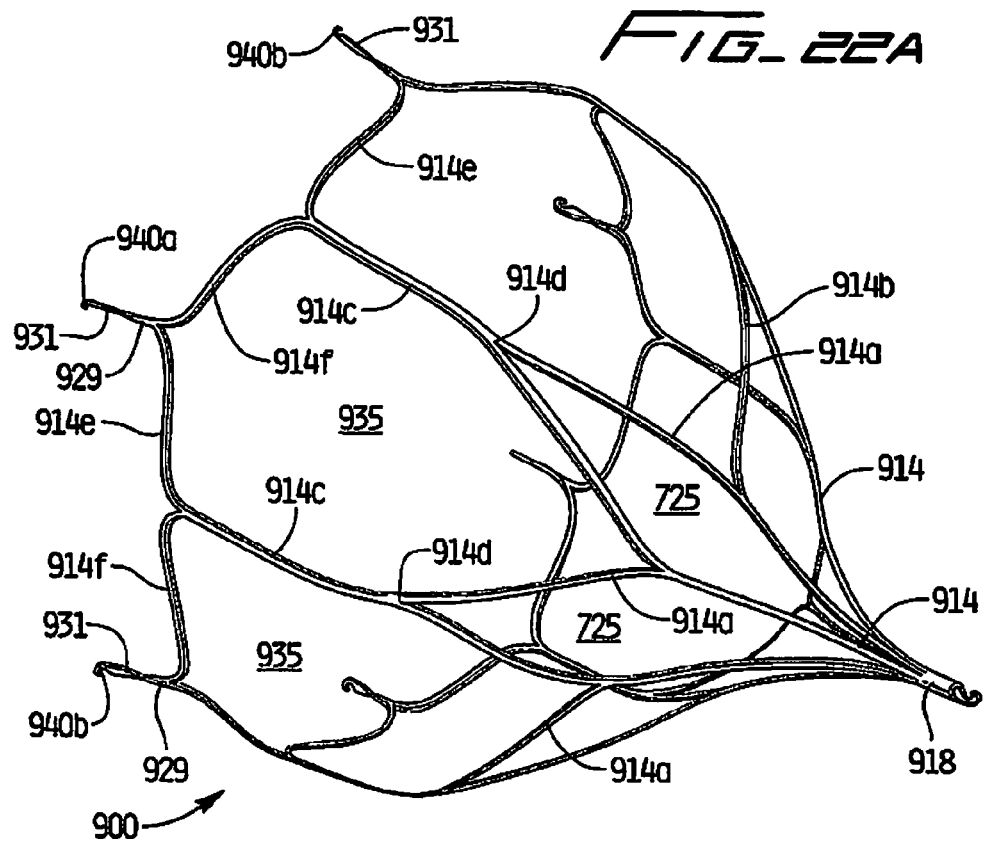
FIG_22A
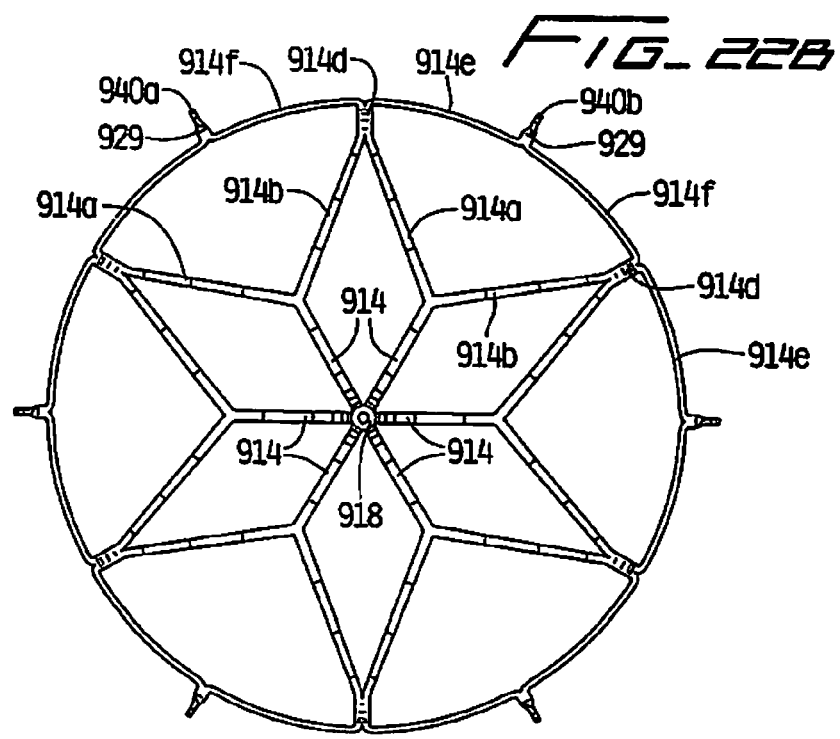
FIG_22B

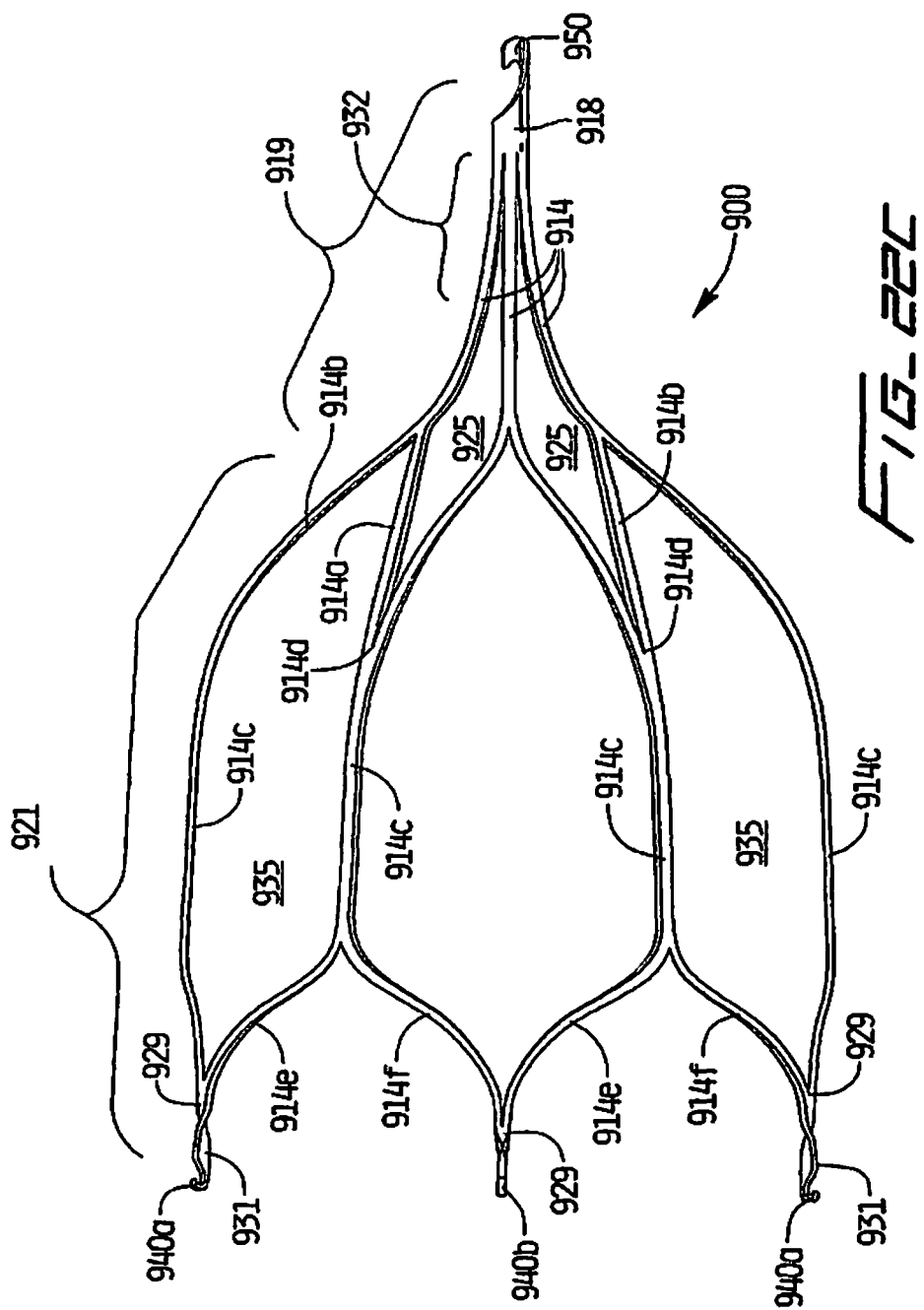

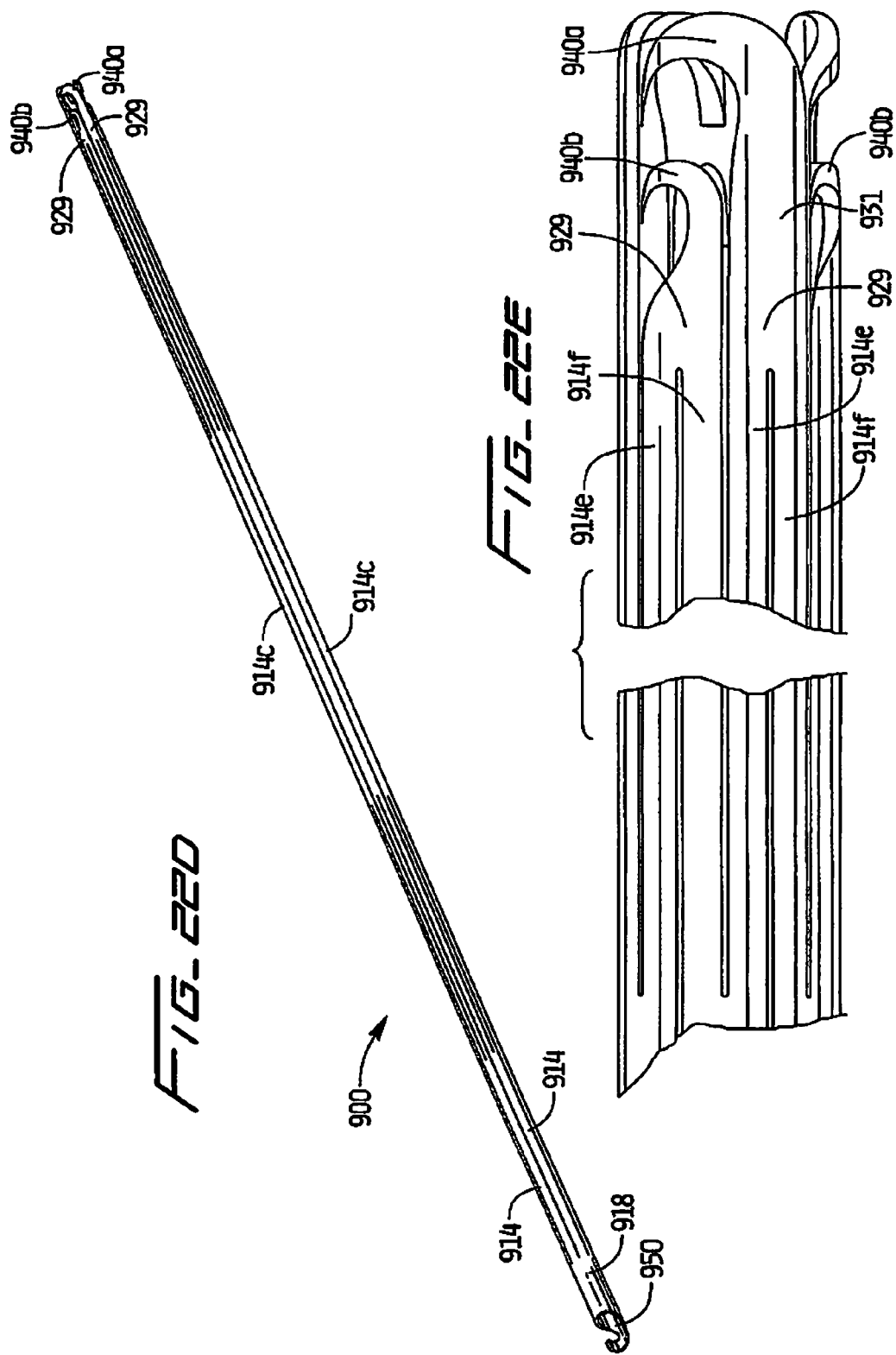

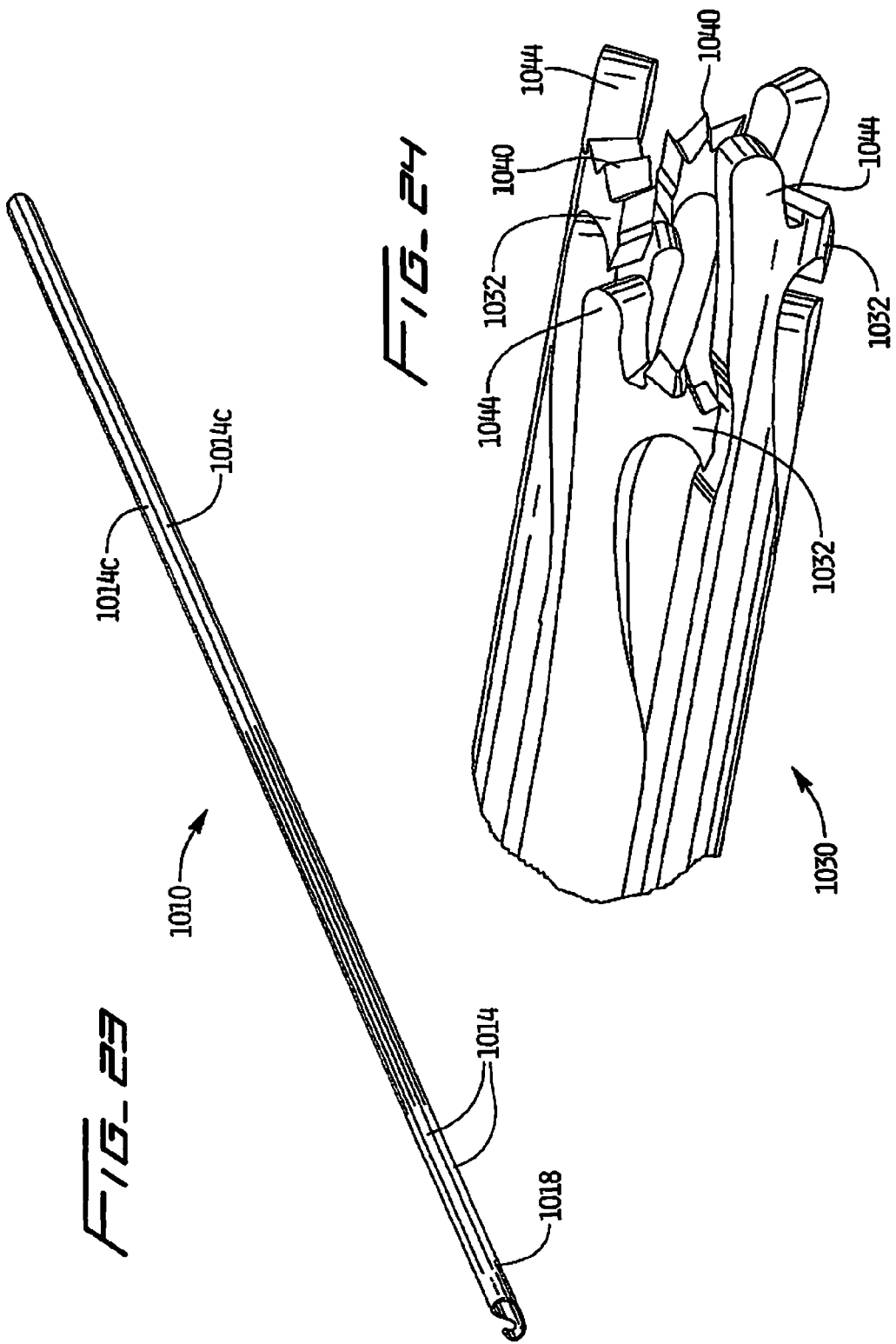

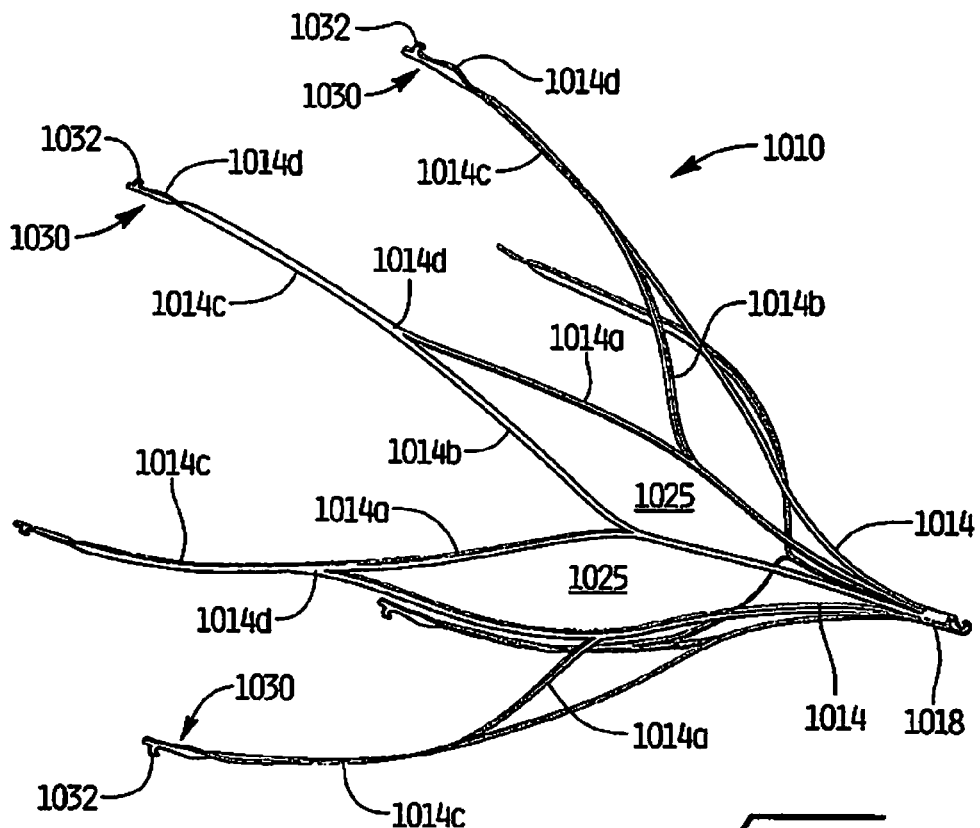
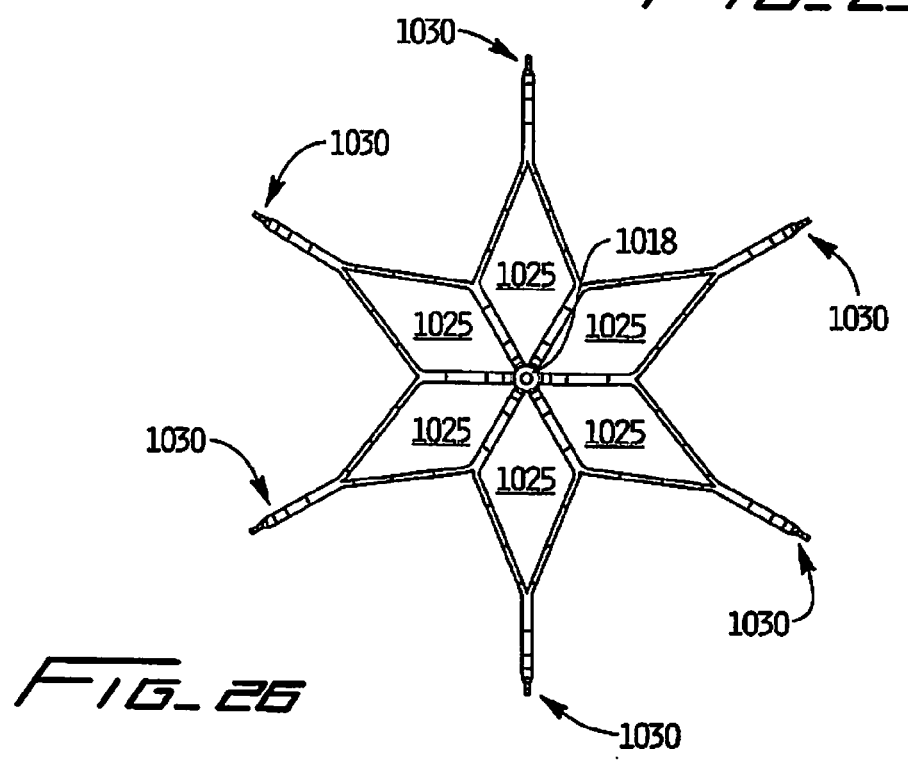

VEIN FILTER

This application is a continuation of prior application Ser. No. 12/770,508, filed on Apr. 29, 2010, now U.S. Pat. No. 8,162,972, which is continuation in part of application Ser. No. 11/978,821, filed Oct. 30, 2007 which is a continuation of application Ser. No. 10/889,429 filed on Jul. 12, 2004, now U.S. Pat. No. 7,704,266, which claims priority from provisional application Ser. No. 60/572,274 filed May 18, 2004, and which is a continuation in part of application Ser. No. 10/805,796 filed on Mar. 22, 2004, now U.S. Pat. No. 7,338,512 which claims priority from provisional application Ser. No. 60/538,379, filed Jan. 22, 2004, and is a continuation in part of application Ser. No. 11/801,547, now U.S. Pat. No. 7,976,562, filed on May 10, 2007, which claims priority from provisional application Ser. No. 60/818,202 filed on Jun. 30, 2006 and which is a continuation in part of application Ser. No. 10/889,429 filed on Apr. 27, 2010. The entire contents of each these applications are incorporated herein by reference.

BACKGROUND

1. Technical Field

This application relates to a vascular filter and more particularly to a vein filter for capturing blood clots within the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. One surgical method of treatment involved major surgery where the size of the vessel lumen was restricted by placement of ligatures or clips around the vein, e.g. the inferior vena cava which transports blood from the lower portion of the body to the heart and lungs. This prevented passage of dangerously large blood clots through the vein to the lungs. However, this approach is an invasive surgical procedure, requiring an abdominal incision and general anesthesia and frequently causing vessel thrombosis and lower extremity swelling. Also, there is a lengthy patient recovery time and additional hospital and surgeon expenses associated with this major surgery. In fact, oftentimes, the patients requiring the surgery are unhealthy and the major surgery and general anesthesia poses a risk in and of itself.

To avoid such invasive surgery, less invasive surgical techniques have been developed. These involve the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Several factors have to be considered in designing vein filters. One factor is that the filter needs to be securely anchored within the vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

It would be advantageous to provide a vein filter that satisfies the foregoing parameters. Namely, such vein filter would advantageously have sufficient anchoring force to retain the filter within the vessel while providing atraumatic contact with the vessel wall, would have a minimized insertion (collapsed) profile to facilitate delivery through the vascular system to the surgical site, and would enable migration of the captured blood clots to the center of the vessel. Moreover, it would also be advantageous to provide a filter that could simplify insertion through the femoral or the right jugular vein or arm into the inferior vena cava.

Additionally, the need for a vein filter in many patients is temporary. In these instances it would be advantageous to provide a vein filter that satisfies the foregoing factors and in addition could be readily removed from the patient. Thus, the filter would advantageously strike the balance of having structure to provide sufficient anchoring while enabling atraumatic removal from the vessel after a period of time. It would further be advantageous if the filter could be removed minimally invasively, e.g. intravascularly.

SUMMARY

The present invention provides in one aspect a vessel filter comprising a first region and a second region, the filter movable between a collapsed position for delivery to the vessel and an expanded position for placement within the vessel. The first region has a filter portion having a converging region to direct particles toward the center of the filter and includes a plurality of spaced apart filter struts. The struts each have a strut width defined as a distance between a first wall and a second wall. A plurality of hooks are at the second region, each of the hooks having a vessel penetrating tip, positioned on a distal end portion of the strut, and having a width greater than the width of the strut from which it extends such that the penetrating tip portion of the hook extends radially beyond the first wall.

In one embodiment, the hooks have a curved end surface. Preferably, the hook includes a heel extending at an angle to a longitudinal axis of the strut. In a preferred embodiment, the penetrating tip extends in a direction toward the first region and the heel extends in an opposite direction.

The filter is preferably formed from a laser cut tube and composed of shape memory material. Preferably the filter includes a retrieval hook having a cutout exposing an internal annular surface, the annular surface dimensioned to receive a portion of a retrieval sheath.

In some embodiments, connecting filter struts extend at an angle from the filter struts to join adjacent filter struts.

In a preferred embodiment, the hooks include a plurality of teeth extending in an opposite direction of the penetrating tip. Preferably, the heel extends radially beyond the second wall of the respective strut.

In another aspect of the present invention, the vessel filter comprises a body made from a single tube, the tube cut to create a plurality of elongated struts forming a filter region and a mounting region of greater transverse dimension. The mounting region includes a plurality of vessel engaging hooks, each of the hooks having a penetrating tip pointing in a direction toward the filter region, a plurality of teeth for engaging the vessel, and a heel extending beyond the teeth in a direction opposite the direction of the penetrating tip.

In one embodiment, the penetrating tip extends substantially parallel to the longitudinal axis of the strut.

In a preferred embodiment, the heel of the hook extends at an angle to the longitudinal axis of the struts in the mounting region. In one embodiment, the heel of adjacent vessel engaging hooks terminate axially spaced. In one embodiment, the heel of one hook is longitudinally aligned with the penetrating tip of an adjacent hook.

The present invention provides in another aspect a vessel filter comprising a first region and a second region, the filter movable between a collapsed position for delivery to the vessel and an expanded position for placement within the vessel. The first region has a filter portion having a converging region to direct particles toward the center of the filter, the first region including a plurality of spaced apart filter struts, the struts each having a strut width defined as a distance between a first wall and a second wall. A plurality of hooks are provided at the second region, each hook having a vessel penetrating tip and a heel, the penetrating tip of one hook longitudinally aligned with a portion of the heel of an adjacent hook.

In one embodiment, the hook has a third and fourth wall and a second width defined between the third and fourth walls, the second width greater than the width of the strut from which it extends such that the penetrating tip portion of the hook extends radially beyond the first wall. In one embodiment, the heel of the hook extends beyond the second wall of the strut. The strut can have a reduced diameter area transitioning into the hook, the reduced area providing a space to accommodate a heel of an adjacent hook. In one embodiment, the penetrating tip of the hook points toward the first region. In one embodiment, the heel has a width less than the width of the respective strut. The hook can have a heel that extends at an angle to the longitudinal axis.

BRIEF DESCRIPTION OF THE DRAWINGS

Preferred embodiment(s) of the present disclosure are described herein with reference to the drawings wherein:

FIG. 1 is a perspective view of a first embodiment of the vein filter of the present invention in the collapsed configuration;

FIG. 2 is an enlarged side view of a portion of the vein filter of FIG. 1;

FIG. 3 is a perspective view of the vein filter of FIG. 1 in an expanded configuration;

FIG. 4A is a side view of the vein filter of FIG. 1 in another expanded configuration;

FIG. 4B is a front view of the vein filter of FIG. 4 in the expanded configuration;

FIG. 5 is a side view of the vein filter of FIG. 3 in the expanded configuration;

FIG. 6A is a close up view of a portion of the struts showing one embodiment of anchoring elements having pointed ends;

FIG. 6B is a close up view of a portion of one of the struts showing another embodiment of anchoring elements in the form of hemispherical cutouts;

FIG. 8 is a side view of the vein filter of FIG. 7;

FIG. 9 is a side view of a portion of the vein filter of FIG. 7 shown in the collapsed configuration;

FIG. 10 is a perspective view of another alternate embodiment of the vein filter of the present invention shown in the expanded configuration;

FIG. 11A is a perspective view of yet another alternate embodiment of the vein filter of the present invention shown in the expanded configuration;

FIG. 11B is a view similar to FIG. 11A showing an alternate embodiment of the hooks;

FIG. 11C is a view similar to FIG. 11A showing another alternate embodiment of the hooks;

FIG. 11D is a view similar to FIG. 11A showing yet another alternate embodiment of the filter of the present invention;

FIG. 11E is a perspective view of the filter of FIG. 11D in the collapsed position;

FIG. 11F is an enlarged view of the retention hooks of FIG. 11D;

FIG. 11G is a perspective view of an alternate embodiment of the filter of FIG. 7 having the retention hooks of FIG. 11D;

FIG. 11H is an enlarged view of the retention hooks of FIG. 11G in the collapsed position;

FIG. 12A is a close up perspective view of an alternate embodiment of an end of the filter having a series of cutouts to receive a retrieval snare;

FIG. 12B is a close up perspective view of an alternate embodiment of an end of the filter having cutouts to receive a retrieval snare;

FIG. 12C is a side view of the embodiment of FIG. 12B showing a retrieval snare placed in one of the cutouts between the coils;

FIG. 13A is a close up perspective view of another alternate embodiment of an end of the filter having a hook to receive a retrieval snare;

FIG. 13B is a perspective view of an end of the filter illustrating another alternate embodiment of the hook to receive a retrieval snare;

FIGS. 13C and 13D are perspective and top views, respectively, of an alternate embodiment of the hook to receive a retrieval snare;

FIG. 13E is a top view of an alternate embodiment of the hook of FIG. 13C;

FIGS. 13F and 13G are perspective and side views, respectively, of another alternate embodiment of the hook to receive a retrieval snare;

FIGS. 13H-13J are side views showing the method steps for engaging the hook of FIG. 13F for removing the filter utilizing a retrieval snare when the snare approaches from one orientation;

FIGS. 13K-13N are side views showing the method steps for engaging the hook of FIG. 13F for removing the filter utilizing a retrieval snare when the snare approaches from an orientation opposite the orientation of FIG. 13H;

FIGS. 14, 15 and 16 illustrate delivery and placement of the vessel filter of FIG. 1 in the inferior vena cava wherein FIG. 14 illustrates initial insertion of the delivery sheath through the femoral vein, FIG. 15 illustrates the delivery sheath being advanced toward the inferior vena cava just below (upstream) the juncture of the renal arteries; and FIG. 16 illustrates the delivery sheath fully withdrawn to place the filter in the expanded placement configuration in the inferior vena cava;

FIG. 17 is a perspective view of one embodiment of a delivery system for the vein filter;

FIG. 18 is an exploded view of the delivery system of FIG. 17;

FIG. 19 is a cross-sectional view showing the engagement of the interlocking rails of the cartridge with the hub;

FIG. 20A is a perspective view of an alternate embodiment of the filter of the present invention having interconnecting struts in the filter portion, the filter shown in the expanded configuration;

FIG. 20B is a front view of the filter of FIG. 20A;

FIG. 20D is a perspective view of the filter of FIG. 20A shown in the collapsed configuration;

FIG. 20E is an enlarged view of an end portion of the filter of FIG. 20D showing the retention hooks;

FIG. 21 is a perspective view of another alternate embodiment of the filter having interconnecting struts in the filter portion;

FIG. 22A is a perspective view of another alternate embodiment of the filter of the present invention having interconnecting struts in the filter portion and in the mounting portion;

FIGS. 22B and 22C are front and side views, respectively of the filter of FIG. 22A;

FIG. 22D is a perspective view of the filter of FIG. 22A shown in the collapsed configuration;

FIG. 22E is an enlarged view of an end region of the filter of FIG. 22D in the collapsed configuration;

FIG. 23 is a perspective view of another alternate embodiment of the vein filter of the present invention in the collapsed configuration for delivery;

FIG. 24 is a close up perspective view of the retention hooks of the filter of FIG. 23 in the collapsed position;

FIG. 25 is a perspective view of the vein filter of FIG. 23 in the expanded configuration;

FIG. 26 is a front view of the filter of FIG. 25;

DETAILED DESCRIPTION OF PREFERRED EMBODIMENTS

Figure 7:
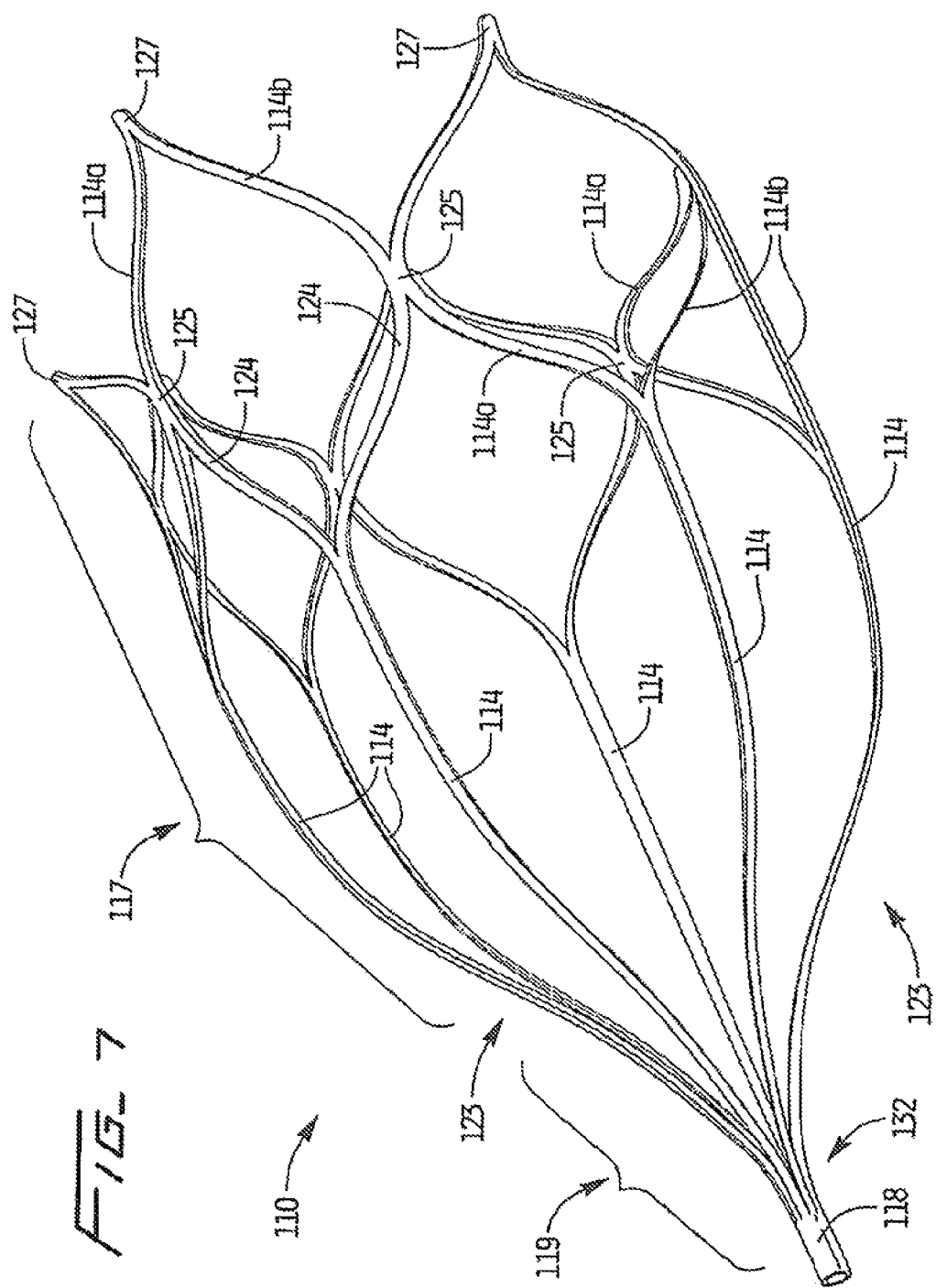
FIG. 7 is a perspective view of an alternate embodiment of the vein filter of the present invention shown in the expanded configuration.

Turning now to the drawings, wherein like reference numerals identify similar or like components throughout the several views, various embodiment of the vein filter of the present invention are described for placement within the inferior vena cava to capture blood clots or other particles which could otherwise pass to the lungs.

The filter is movable from a low profile collapsed configuration to facilitate insertion through the delivery sheath to a larger expanded placement configuration to enable atraumatic engagement with the vessel walls to secure (mount) the filter within the inferior vena cava. The filter is preferably substantially bell-shaped and preferably has a flared or mounting region (portion/section) and a filtering region (portion/section). As described in more detail below, the filtering portion has inwardly directed struts, terminating in a converging region, thereby directing particles toward the central axis of the filter. By directing the particles to the center, they will be exposed to greater blood flow which improves dissolution of the particles. The other portion increases in transverse dimension to form a flared region. The flare provides less contact area than a straight region, resulting in less tissue ingrowth to facilitate removal of the filter if desired. The flare also reduces the chance of vessel distortion if inserted into a curved vena cava.

Turning now to details of the filter of the present invention and with initial reference to FIGS. 1 and 2, the filter is designated generally by reference numeral 10 and is shown in a collapsed configuration for delivery. Filter 10 is preferably formed from a single tube 11. In a preferred embodiment, the filter 10 is composed of shape memory material, such as Nitinol, a nickel titanium alloy, or elgiloy, however, other materials such as stainless steel are also contemplated. A plurality of cutouts 12 are formed in the filter 10, preferably by laser cutting although other techniques are contemplated. In the illustrated embodiment, six elongated cutouts are formed, creating six strips or struts 14 of substantially uniform width separated by the cutouts 12 and extending from tubular portion 18.

The collapsed configuration of filter 10 reduces the overall profile to facilitate delivery to the site. The diameter or transverse dimension of filter 10 in the collapsed configuration is represented by reference D1 and preferably is about 2 mm and more preferably about 1.7 mm. Other dimensions are also contemplated. The diameter or transverse dimensions of the filter in the expanded placement configurations (e.g. FIGS. 4A and 5) is greater than the diameter or transverse dimension D1 in the collapsed (delivery) configuration. The filter is thus preferably dimensioned for insertion through a 6 French delivery system and through a 6 French catheter.

FIGS. 3-5 illustrate the expanded placement configuration of the filter 10. Filter 10 is generally bell-shaped in configuration. Filter 10 has a flared region 17 and a converging region 21 at the filtering section 19. The transverse dimension of the filter at flared (or mounting/anchoring) region 17 is thus greater than the transverse dimension at filtering section 19. In larger vessels, the filter can expand to a diameter D2 shown in FIG. 5. In smaller vessels, the filter expands to a smaller diameter, e.g. D3, shown in FIG. 4. Diameters (or transverse dimensions) D2-D3 preferably range from about 18 mm to about 32 mm, depending on the internal diameter of the vessel wall as will be explained in more detail below. Other dimensions are also contemplated.

The elongated struts 14 are spaced apart as shown and extend at an angle away from the longitudinal axis L of filter 10 in region 17 to provide a flare. Preferably, this angle or taper is about 10°, although other dimensions are contemplated. In the filtering region 19, beginning at an intermediate portion of the filter (the transition between the first and second regions 17, 19) the struts 14 curve or bend inwardly (region 23) toward the longitudinal axis and then extend inwardly at an angle to the tubular portion 18, thereby forming an angle with the longitudinal axis. In the illustrated embodiment, when expanded, the six struts 14 are shown spaced approximately 60 degrees apart. It is also contemplated that a fewer or greater number of struts could be provided and spacing other than 60 degrees be provided.

In the expanded placement configuration, a portion of the each elongated strut 14 has an outer surface 20 for engagement with the vessel wall to retain the filter 10 in position in the vessel. This region is angled with respect to the longitudinal axis. The outer surface 20 of struts 14 could be roughened to enhance engagement. Alternatively, a plurality of atraumatic tabs, barbs or other penetrating members can extend from the outer surface 20 of the struts 14 to engage the vessel wall to retain the filter. FIGS. 6A and 6B show examples of such retention features. In FIG. 6B, the filter has a series of hemispherical cutouts 152 formed along the length of the struts 154 forming pointed edges 156 to engage the vessel wall. The cutouts 152 can be formed along the length of the strut 154 or alternatively be formed only along a portion of the length. The cutouts can also be formed on fewer than all the struts.

In the embodiment of FIG. 6A, the filter has anchoring elements 162 formed by cutouts 163 at the ends of the struts 164. Anchoring elements 162 have pointed ends 165. In the collapsed configuration the anchoring elements 162 and their pointed ends 165 are aligned with the struts 164, substantially parallel with the longitudinal axis of the filter to maintain a reduced profile. When the filter moves to the expanded configuration, the pointed ends 165 face outwardly as shown in FIG. 6A. Anchoring elements 162 can be placed in the end regions of the strut or in other locations. The anchoring elements can also be placed in the opposite direction shown.

In the embodiment of FIG. 11A, the struts 174 of filter 170 terminate in hooks 172 which extend substantially perpendicular from the strut. Hooks extend from the substantially V-shaped region 179 formed by the joining of connecting struts 174a, 174b. In the alternate embodiment of FIG. 11C, struts 184 of filter 180 also terminate in substantially perpendicular hooks 182, however this arrangement is achieved by torquing the connecting struts 184a, 184b at the curved region 185 so the hooks bend out of the plane. As shown, hooks 182 extend from V-shaped region 189 formed by the connecting struts 184a, 184b. In the alternate embodiment of FIG. 11B, the hooks 192 of filter 190 (having struts 194) lie in the plane of the connecting struts 194a, 194b, flush with the width surface "w" of the V-shaped region 199 of connecting struts 194a, 194b.

In the alternate embodiment of FIGS. 11D-11F, the hooks 302 lie in the same plane as the connecting struts 304a, 304B of struts 310 as in FIG. 11B; however the hooks of filter 301 are of two different sizes. More specifically, a first set of hooks 302a is larger than a second set of hooks 302b. Preferably when formed in a laser cut tube, hooks 302a are formed so that they occupy a region equivalent to the transverse dimension of two adjacent struts. For example, in the collapsed configuration, hook 302a occupies a region (dimension) of four connecting struts while smaller hook 302b would only occupy the region (dimension) of two connecting struts. Smaller hooks 302b are spaced axially inwardly with respect to larger hooks 302a to minimize the collapsed profile (transverse dimension) of the filter when collapsed for insertion. In this preferred embodiment, smaller hooks 302b occupy the space created by the larger hooks 302a so they can be considered as nesting within larger hooks 306a. Stated another way, each hook 302b has an outer surface 307 which conforms (follows the contour) to an inner surface 309 of a hook 306a. The penetrating tips 306a, 306b in hooks 302a, 302b, respectively, penetrate the tissue to retain the filter, preferably temporarily.

The aforedescribed hooks 172, 182, 192, 302 (as well as the hooks described below) can be used with any of the disclosed embodiments (see e.g. FIG. 11G). Such hooks can also be formed or placed on fewer than all the struts.

Referring back to FIGS. 3-5, the filter portion of filter 10 will now be discussed. As noted above, the filtering section of filter 10 at a first end of the filter is designated generally by reference numeral 19 and includes the converging region 21. Filtering section 19 extends from the flared region 17, and extends toward the central longitudinal axis L of the filter 10 and converges at portion 32 into tubular portion 18. At the transition region between the filtering and flared regions 19, 17, struts 14 bend inwardly (region 23), then extend radially inwardly toward the tubular portion 18, and transition to the tubular portion 18. The tubular portion 18 and converging region 19 of the filter 10 are spaced both axially outwardly and radially inwardly from the bend regions 23 of the strut 14. (Axially outwardly is represented by arrow "a" and radially inwardly is represented by arrow "b" in FIG. 4A). The filter is designed to direct particles to the center of the filter and vessel. (Trapping the particles at the center rather than the edges of the filter is more desirable because there is less blood flow at the edges of the vessel and greater blood flow at the center to better dissolve the particles.) For clarity, not all of these sections of each strut 14 are labeled in the drawings, it being understood that the non-labeled struts can have the same configurations.

Turning now to the flared or mounting (anchoring) region 17, each strut 14 is divided into two connecting strut portions 14a, 14b. Preferably, each strut portion 14a, 14b is about one half the width of the undivided strut 14, although other widths are contemplated. The strut portions 14a, 14b of each divided strut 14 extend in opposite directions and include a curved region 25 as the strut portions 14a, 14b each extend toward respective strut portion 14a or 14b of an adjacent strut. That is, strut portions 14a, 14b form connecting portions to connect adjacent struts 14 as connecting strut 14a of one strut is connected to connecting strut 14b of an adjacent strut. Connecting strut portion 14a on one strut and portion 14b of another strut converge at end region 29 of the filter and form a substantially V-shaped region. Six such V-shaped end portions are preferably formed, each portion connecting adjacent struts. Note that although all six struts 14 are shown interconnected, it is also contemplated that fewer than all the struts can be interconnected.

Note the designations of longitudinal, angled, curved, bowed, connected, joined, interconnected, connecting strut, etc. in the illustrated embodiments refer to the same integral strut and are divided into such regions for ease of understanding.

It should be understood that the elongated struts 14 bend as they move from their collapsed position to their expanded placement configuration. Therefore, stated another away, the filter 10 can be viewed as having a filtering section 19 at a first end extending from the tubular portion 18. As viewed, each of the struts 14 emerges from the tubular portion 18 at an angle that extends outwardly away from the center to transition to curved portions 23. The curved portions 23 extend outwardly away from the longitudinal axis forming a flare or region of progressively increasing transverse dimension. In this flared region 17, near a second end of the filter (opposite the end containing tubular portion 18), the struts 14 are interconnected by connecting struts 14a, 14b that curve inwardly toward the connecting strut 14a or 14b of an adjacent strut to form a substantially V-shaped end portion.

In the placement (expanded) configuration, the filter 10 moves towards its memorized position and the extent it returns to its fully memorized position will be dependent on the size of the vessel in which the filter 10 is inserted. (The larger the vessel, the closer the filter comes to returning to it's fully memorized position). This can be understood by comparing FIGS. 4A and 5 which illustrate by way of example two possible expanded dimensions of the filter; FIG. 4A showing expansion to a smaller dimension occurring in smaller diameter vessels and FIG. 5 showing expansion to a larger dimension occurring in larger diameter vessels.

To enable movement between an expanded and collapsed configuration, the filter tube of the embodiments described herein is preferably made of shape memory metal material, such as Nitinol, a nickel titanium alloy. The memorized configuration of the filter 10 is shown in FIG. 1. To facilitate passage of the filter 10 through the lumen of the delivery sheath 100 (shown in FIG. 14 in conjunction with the method of insertion) and into the vessel, cold saline can be injected into the delivery sheath or catheter 100 and around the filter 10 in its collapsed position within the delivery sheath 100. This shape memory material characteristically exhibits rigidity in the austenitic state and more flexibility in the martensitic state. The cold saline maintains the temperature dependent filter 10 in a relatively softer condition as it is in the martensitic state within the sheath. This facilitates the exit of filter 10 from the sheath 100 as frictional contact between the filter 10 and the inner surface of the sheath would otherwise occur if the filter was maintained in a rigid, i.e. austenitic, condition.

Once ejected from the delivery sheath or catheter 100, the filter is no longer cooled and is exposed to the warmer body temperature, which causes the filter 10 to return towards its austenitic memorized configuration.

The filter 10 (and other filters described herein) can be inserted through the jugular vein in the neck of the patient or through the femoral vein in the leg of the patient or the arm. The filters can also be placed in the superior vena cava.

FIGS. 14-16 illustrate delivery and placement of the filter 10, by way of example, in the inferior vena cava. Delivery catheter 100 is inserted through the femoral vein "f" and advanced through the iliac arteries into the inferior vena cava. Delivery catheter would be withdrawn once the tip of the sheath is adjacent the structure so that withdrawal of the sheath would place the filter in the desired location of FIG. 16. Tubing 104 and valve assembly 106 enable saline injection. Delivery catheter 100 is withdrawn to enable filter 10 to be warmed by body temperature to transition to the expanded placement configuration. The other filters described herein could be inserted in the same manner. Note it is implanted in the orientation such that filter section 19 is downstream of the flared section 17. This enables blood clots or other particles to be directed to the center of the filter section by the angled struts. Thus the direction of insertion, e.g. upstream or downstream direction, will determine how the filter is to be positioned in the delivery catheter.

In an alternate embodiment of the filter, the strut width can vary. For example, the struts can be wider at the flared region than at the filtering portion. This is preferably achieved by removing material to create the thinner portions. These thinner portions increase the flexibility of the filter for forming the angled and curved portions upon deployment. Alternatively, the filter can have struts which are thinner, rather than wider, at the flared region, than at the angled and curved regions of the filtering portion. This would provide more stability at the curved regions. The adjustment of the widths is designed to strike a balance between stability and flexibility of the various regions of the filter. Thus, other width variations are contemplated such as making multiple width changes within each strut and/or in different struts.

FIGS. 7-9 illustrate an alternate embodiment of the filter, designated by reference numeral 110. Filter 110 is similar to filter 10 except for end region 121. That is, like filter 10, filter 110 has a filtering region 119 which extends from the flared (anchoring/mounting) region 117, and extends toward the central longitudinal axis L of the filter 110 and converges at portion 118. Struts 114 bend inwardly toward the longitudinal axis of the filter 10 at region 123. For clarity, not all of these sections of each strut 114 are labeled in the drawing, it being understood that the non-labeled struts can have the same configurations. The flared region 117 as in filter 10 is of an angle preferably about 8 degrees although other angles are contemplated.

The end region 121 of filter 110 where the struts 114 interconnect differs from filter 10. In filter 110, the struts 114 are interconnected by connecting strut portions 114*a*, 114*b* that curve outwardly away from the central axis and then inwardly toward each other to form a substantially V-shaped end portion 127. At the outward curved or bowed portion 124, the connecting struts are joined to connecting struts of adjacent struts 114 (region 125). Thus, a closed geometric shape 133 is formed as shown. The closed shape as shown is substantially oval in configuration, although other shapes are contemplated. Six such closed geometric shapes are preferably formed, each connecting adjacent struts, although fewer closed shapes are contemplated if fewer than all the struts are interconnected. Also, the length of the region 125 where the struts are joined can be shorter or longer than that shown, thereby changing the configuration of the closed geometric shape (e.g. making it longer or shorter).

Stated in other words, each strut 114 divides into two connecting strut portions 114*a*, 114*b* which initially extend outwardly from each other. As each strut extends outwardly, the strut portion 114*a* joins the strut portion 114*b* of an adjacent strut at region 125. After this joined region 125, the strut portions 114*a* and 114*b* which emanate from the same strut extend inwardly towards each other and are joined at their ends into a substantially V-shaped end, designated by reference numeral 127.

The collapsed configuration of filter 110 is shown in FIG. 9 with cutouts 112 forming six struts 114. Regions 113 illustrate where struts 114 divide.

In the alternate embodiment of FIG. 10, filter 150 resembles filter 10 of FIG. 1 except for the additional connecting struts or ribs 152. These ribs increase the stability of the filter 150. As shown, the two ribs 152 extend from adjacent struts 154 and curve inwardly towards each other and are joined at region 156 (forming a V-like connection). The ribs 152 can be arranged so they are axially aligned as in FIG. 10 or alternatively can be staggered i.e. spaced axially (not shown). Also, the ribs can be placed between fewer than all the struts and the ribs can be utilized with any of the foregoing embodiments. Note that the ribs are preferably integrally formed with the filter, formed by the laser cutting process mentioned above; however, alternatively the ribs can be attached to the struts. Struts 154 divide into connecting struts 154*a*, 154*b* in the embodiment of FIG. 1.

FIGS. 11G and 11H illustrate an alternate embodiment of the filter of FIG. 7 having the hooks of filter 301 of FIG. 11D. Filter 350, like filter 110, has struts 354 which are interconnected by connecting strut portions 354*a*, 354*b* that curve outwardly then inwardly toward each other to form V-shaped portions 357, terminating in hooks 356. As in FIG. 11D, large hooks 356*a* alternate with axially offset smaller hooks 356*b* and are identical to hooks 306*a*, 306*b* of FIG. 11D.

In another embodiment, the ribs could curve radially outward near their tips, thus contacting the vessel wall and acting as a retaining mechanism.

FIG. 20A illustrates an alternate embodiment of the filter of the present invention. In this embodiment, the struts are interconnected at the filtering region rather than at the flared mounting (anchoring) region. This creates closed geometric shapes at the filtering region to enhance the clot capturing capability of the filter. Also, by providing the interconnection more forward (downstream) in the filter, i.e. in the filtering region (filtration zone), linear movement of the filter is facilitated to enhance removal of the filter.

Figure 20C:
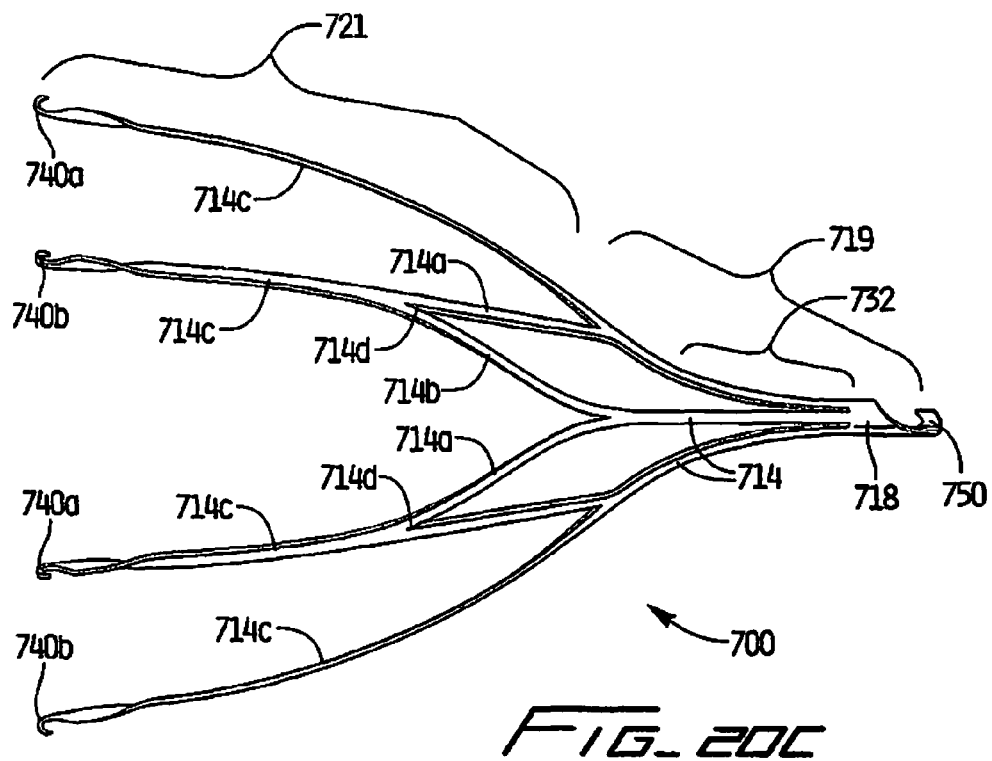
FIG. 20C is a side view of the filter of FIG. 20A.

Turning first to FIGS. 20A and 20C, bell-shaped filter 700 has a filtering region 719 and a flared anchoring (mounting) region 721 of greater transverse dimension. Flared region 721 is preferably at an angle of about 8 degrees to about 14 degrees with respect to the longitudinal axis of the filter, although other angles are contemplated. In this flared region 721, the transverse dimension increases towards the anchoring end of the filter 700 so that as in the other embodiments disclosed herein, the terminal end of the filter at region 719 has a smaller transverse dimension than at the opposing terminal end at region 721. The filtering region 719 extends from the flared region 721 toward the longitudinal axis of the filter 700 and converges at portion 732 into tubular portion 718 at the filter end portion of filter 700.

Filtering region 719 has six struts 714 curving outwardly from tubular portion 718. Each filter strut or strut portion 714 extends radially from tubular portion 718 and divides into two connecting filter struts or strut portions 714a, 714b (preferably of equal width) that angle way from each other (in different directions) to extend to the connecting strut portion of an adjacent strut 714. Thus, connecting strut portion 714a of one strut 714 interconnects with the connecting strut portion 714b of an adjacent strut at joining region 714d. This forms closed geometric shapes 725, preferably substantially diamond shaped in configuration. For clarity, not all of the identical parts are labeled in the drawing. In the illustrated embodiment, preferably six struts are provided forming twelve interconnecting struts, however a different number of struts and closed geometric shapes can be provided. Also, fewer than all of the struts could be interconnected. Although preferably the struts 714 divide into connecting struts 714a, 714b of half the width, other dimensions are contemplated.

After convergence of strut portions 714a, 714b at joining region 714d, it transitions into elongated mounting strut portions 714c which form flared mounting or anchoring region 721. The length of the strut portions 714c in the anchoring region 721 can vary, with increased/decreased length increasing the flexibility/rigidity of the struts. The thickness of the strut portions can also vary to affect flexibility/rigidity.

In one embodiment, the strut portions 714c terminate in hooks 740a, 740b similar to hooks 302a, 302b of FIG. 11D. That is, hooks 740a and 740b lie in the plane of the struts 714c and hooks 740a are larger than hooks 740b, formed so they occupy a region equivalent to the transverse dimension of two adjacent struts. Smaller hooks 740b nest within larger hooks 740a as described above in conjunction with hooks 302a, 302b. Note that smaller hooks 740b are spaced axially (inwardly) of hooks 740a as well as spaced axially with respect to each other as represented by the arrows in FIG. 20F designating the three different distances E1, E2 and E3 in the developed view, presented for ease of understanding since the hooks are formed from a tube. Other hook designs could alternatively be provided, including the various hook embodiments described herein.

The tubular portion 718 is preferably in the form of a retrieval hook as described herein with respect to the other embodiments, and preferably in the form of retrieval hook 290 of FIG. 13F. Other retrieval structure can also be utilized.

In the alternate embodiment of FIG. 21, the filter is designated generally by reference numeral 800 and has a filtering region 819 and a flared anchoring (mounting) region 821. The filter 800 differs from filter 700 in the additional joining regions of the connecting struts. More specifically, filter struts 814 extend radially from tubular portion 818, in a similar manner as struts 714 of FIG. 20A. Struts 814 divide into connecting struts or strut portions 814a, 814b, extending in different directions, and then join at first joining regions 814c to a connecting strut of an adjacent strut 814. Emanating from joining regions 814c, connecting struts or strut portions 814f, 814g, extend in different directions, away from each other, to connect to another adjacent strut 814f or 814g at second joining regions 814d. At regions 814d, the mounting struts or strut portions 814h extend longitudinally to form the flared mounting or anchoring region 821. The interconnecting struts preferably form a first set of substantially diamond shaped closed geometric shapes 830 as shown and a second set of substantially hexagonal shaped closed geometric shapes 832. Other shapes are contemplated as are a different number of struts 814, interconnecting struts, and closed geometric shapes. For clarity, not all identical parts are labeled in the drawings.

At the terminal ends of the struts 814 at the mounting portion 821, retention hooks are provided. Hooks 840a, 840b as shown are identical to hooks 740a, 740b of FIG. 20. Retrieval hook 850 at the tubular end portion 818 of the filtering end portion of filter 800 is preferably identical to retrieval hook 750 of filter 700. Other hook designs and retrieval structure could alternatively be utilized.

FIGS. 23-28 illustrate an alternate embodiment of the filter of the present invention, designated generally by reference numeral 1010. Filter 1010 is substantially identical to filter 700 of FIGS. 20A-20E except for the retention hooks. Filter 1010 has struts interconnected in the filtering region and not in the flared mounting (anchoring) region as in filter 700. This creates closed geometric shapes at the filtering region to enhance the clot capturing capability of the filter. The mounting region is devoid of such closed geometric shapes as it is devoid of interconnecting or connecting struts. This facilitates removal.

Filter 1010 is substantially bell shaped and has a filtering region 1012 and a flared anchoring (mounting) region 1024 of greater transverse dimension. Flared region 1024 is preferably at an angle of about 8 degrees with respect to the longitudinal axis of the filter, although other angles are contemplated. In this flared region 1024, the transverse dimension increases towards the anchoring end of the filter 1010 so that as in the other embodiments disclosed herein, the terminal end of the filter at region 1019 has a smaller transverse dimension than at the opposing terminal end at region 1021. The filtering region 1012 extends from the flared region 1024 toward the longitudinal axis of the filter 1010 and converges at portion 1022 into tubular portion 1018 at the filter end portion of filter 1010.

Filtering region 1019 preferably has six struts 1014 curving outwardly from tubular portion 1018. Each filter strut or strut portion 1014 extends radially from tubular portion 1018 and divides into two connecting (interconnecting) filter struts or strut portions 1014a, 1014b (preferably of equal width) that angle way from each other (in different directions) to extend to the connecting strut portion of an adjacent strut 1014. Thus, connecting strut portion 1014a of one strut 1014 interconnects with the connecting strut portion 1014b of an adjacent strut at joining region 1014d. This forms closed geometric shapes 1025, preferably substantially diamond shaped in configuration, although other shapes are contemplated. For clarity, not all of the identical parts are labeled in the drawing. In the illustrated embodiment, preferably six struts are provided forming twelve interconnecting struts, however a different number of struts and closed geometric shapes can be provided. Also, fewer than all of the struts could be interconnected. Although preferably the struts 1014 divide into connecting struts 1014a, 1014b of half the width, other dimensions are contemplated.

After convergence of strut portions 1014a, 1014b at joining region 1014d, it transitions into elongated mounting strut portions 1014c which form flared mounting or anchoring region 1024. The length of the strut portions 1014c in the anchoring region 1024 can vary, with increased/decreased length increasing the flexibility/rigidity of the struts. The thickness of the strut portions can also vary to affect flexibility/rigidity.

Figure 28:
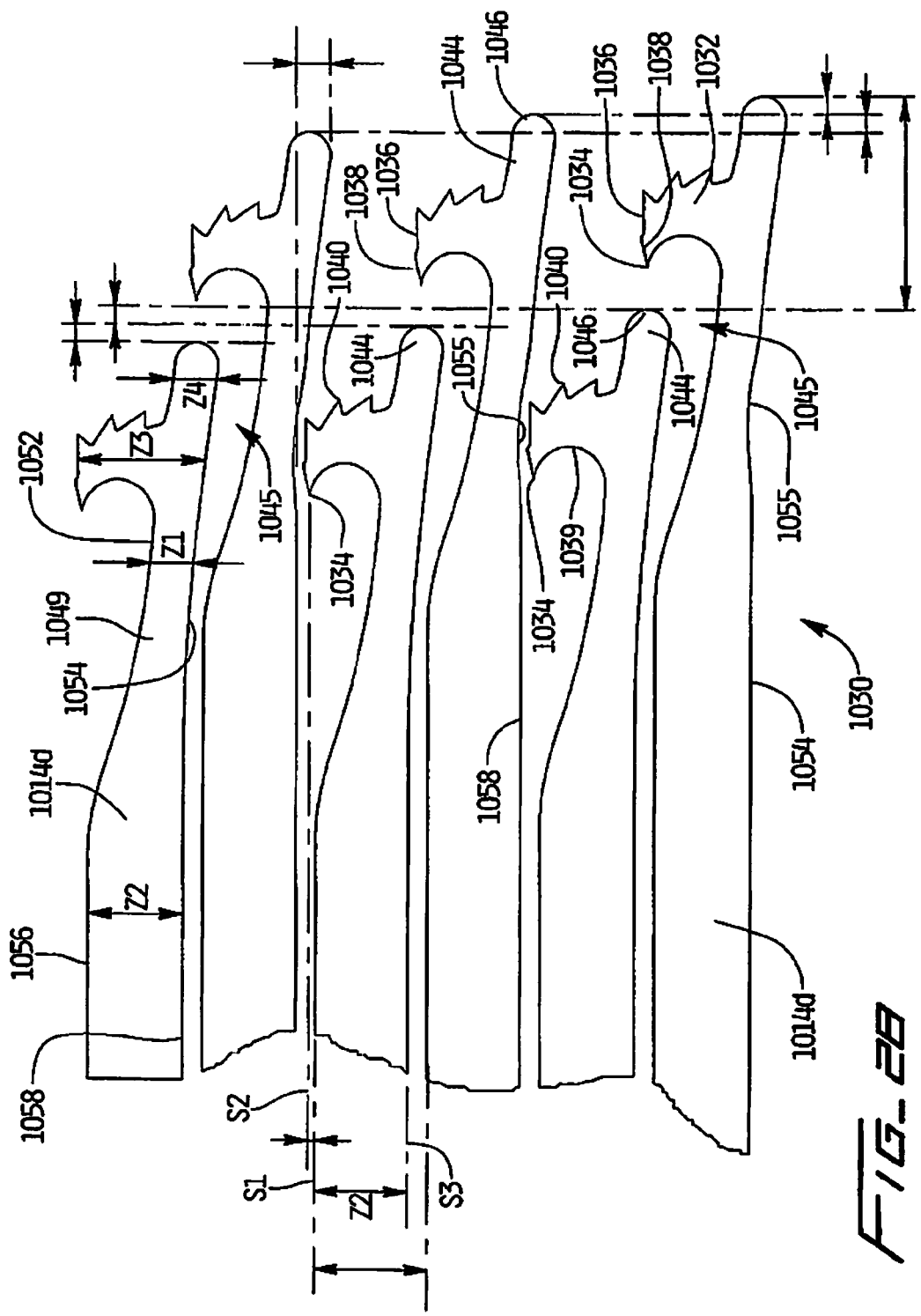
FIG. 28 is an enlarged developed view of the end portion of the filter of FIG. 27.

Preferably, the strut portions 1014c terminate in hook portions 1030. Hook portions 1030 in this embodiment are preferably of substantially the same size. In the preferred embodiment, the hook portions or the struts from which they extend have different lengths so that the distalmost end of the hook portions 1030 terminate at different axial positions. Stated another way, the hooks are staggered in an axial direction so the struts terminate at different points. FIG. 28 illustrates the six different distances, in the developed view, presented for ease of understanding since the hooks are formed from a tube.

Hook portions 1030 lie in the plane of a distal portion 1014d of the struts 1014c. That is, the distal portion 1014d of the strut 1014c twists out of the plane of the remaining portion of the strut, with the hooks lying in the plane of the distal portion.

Hook portions 1030 includes a hook 1032 having a penetrating tip 1034 preferably pointing toward a proximal portion (filter region) of the filter 1010. A top wall 1036 of the hook 1032 has a slight step 1038. The penetrating tip 1034 extends about a curved wall 1039. The penetrating tip 1034 in the illustrated embodiment extends substantially parallel to a longitudinal axis L1 of the struts portion 1050. Opposite the curved wall 1039 on hook 1032 are a plurality of teeth 1040, with points or edges facing in a distal direction, opposite the direction of the penetrating tip 1034. Teeth 1040 engage the vessel wall to provide additional retention to prevent movement of the implanted filter in the caudal direction. A heel 1044 is formed on a distal end of the hook portion 1030, terminating in a curved surface 1046 and extending distally beyond the hook 1032. Heel 1044 extends past the hook 1032 to function as a stop to prevent the filter strut portions from going through the vessel wall. Hook portion 1030 also has a reduced width dimension Z1 which transition from the strut 1014d to the hook 1032. For clarity, only some of the hooks and hook portions are labeled in FIG. 28.

Preferably hook portions 1030 somewhat nest within an adjacent hook portion. More specifically, the strut of portion 1030 has a reduced area 1049 (with width dimension Z1) which forms a gap 1045 to receive a portion of heel 1044 of an adjacent hook portion 1030. In this configuration, a portion of the heel 1044 of the hook portion 1030 is in general longitudinal alignment with a penetrating tip 1034 of an adjacent hook as described below.

The strut 1014d at the reduced area portion 1049 has a first wall 1052 and a second wall 1054 forming a width Z1 defined as the distance or space between the walls 1052, 1054. The strut 1014d adjacent the reduced area 1049 has a first wall 1056 and a second wall 1058, forming a width Z2, defined as the distance or space between walls 1056, 1058. Line S1 represents this first wall 1056 of strut 1014d. As can be appreciated, the hook 1032 has a height Z3 greater than height Z2 such that it extends widthwise beyond the height of the first wall 1052. In other words, the penetrating tip 1034 extends radially beyond the Line S1, illustrated by line S2 (extrapolated from the perpetrating tip 1034). By way of example, width Z1 could be between about 0.013 inches to about 0.019 inches, and preferably about 0.016 inches, width Z2 could be between about 0.025 inches to about 0.035 inches, and preferably about 0.030 inches, width Z3 could be about 0.035 inches to about 0.045 inches, and preferably about 0.040 inches, and width Z4 at the heel 1044 could be between about 0.011 inches to about 0.017 inches, and preferably about 0.014 inches. It should be understood that other dimensions are also contemplated.

Line S3 represents the second wall 1058 extrapolated in a proximal direction. As can be appreciated, the heel 1044 extends widthwise beyond the line S3 and width of the second wall 1054. Wall 1058 also includes a slight indentation 1055 to accommodate the penetrating tip portion 1034 of the adjacent hook 1032.

The tubular portion 1018 is preferably in the form of a retrieval hook as described herein with respect to the other embodiments, and preferably in the form of retrieval hook 290 of FIG. 13F. Other retrieval structure can also be utilized.

FIG. 22 illustrates an alternate embodiment of the filter of the present invention. In this embodiment, the struts are interconnected at the filtering region (filtration zone) and at the flared mounting (anchoring) region. These interconnecting struts at the filtering region enhance the clot capturing capability of the filter. The interconnection at the mounting region enhances the stability of the filter and the vessel retention capability by reducing the flexibility of the struts.

Referring to FIGS. 22A and 22C, bell-shaped filter 900 has a filtering region 919 and a flared anchoring (mounting) region 921 of greater transverse dimension. Flared region 921 is preferably at an angle of about 8 degrees with respect to the longitudinal axis of the filter, although other angles are contemplated. In this flared region 921, the transverse dimension increases towards the anchoring end of the filter 900 so the terminal end of the filter at region 919 has a smaller transverse dimension than the opposing terminal end at region 921. The filtering region 919 extends from the flared region 921 toward the longitudinal axis of the filter 900 and converges at portion 932 into tubular portion 918 at the filter end portion of filter 900.

Filtering region 919 has six struts 914 curving outwardly from tubular portion 918. Each elongated filter strut or strut portion 914 extends radially from tubular portion 918 and divides into two connecting filter struts or strut portions 914a, 914b (preferably of equal width) that angle way from each other (in different directions) to extend to the connecting strut portion of an adjacent strut 914. Thus, connecting strut portion 914a of one strut 914 interconnects with the connecting strut portion 914b of an adjacent strut at joining region 914d. This forms closed geometric shapes 925, preferably substantially diamond shaped in configuration. For clarity, not all of the identical parts are labeled in the drawing. In the illustrated embodiment, preferably six struts are provided forming twelve interconnecting struts in the filtering region, however a different number of struts and closed geometric shapes can be provided. Also, fewer than all of the struts could be interconnected. Although the struts 914 can divide into connecting struts 914a, 914b of half the width, other dimensions are contemplated such as equal to the width.

After convergence of strut portions 914a, 914b at joining region 914d, it transitions into elongated mounting strut portions 914c which form flared mounting or anchoring region 921. The length of the mounting strut portions 914c in the anchoring region 921 can vary, with increased/decreased length increasing the flexibility/rigidity of the struts. The thickness of the strut portions can also vary to affect flexibility/rigidity. Each strut 914c divides into two connecting mounting strut portions 914e, 914f. Each strut portion 914e, 914f can be one half the width of the undivided strut 14, although other widths are contemplated such as equal to the width. The strut portions 914e, 914f of each divided strut 914c extend in opposite directions and include a curved region as the strut portions 914e, 914f each extend toward respective strut portion 914e or 914f of an adjacent strut. That is, strut portions 914e, 914f form connecting portions to connect adjacent struts 914c as connecting strut 914e of one strut is connected to connecting strut 914f of an adjacent strut. Connecting strut portion 914e on one strut and portion 914f of another strut converge at end (joining) region 929, as closed geometric shapes 935 are formed. End region 929 has an elongated region (or hook strut) 931 and preferably terminates in hooks described below. Note that although all six mounting struts 914 are shown interconnected, it is also contemplated that fewer than all the struts can be interconnected.

Thus, as can be appreciated, the elongated struts have a first angled region of interconnecting (connecting) struts 914a, 914b in the filtering region 919 and a second angled region of interconnecting (connecting) struts 914e, 914f in the mounting region 921. The region of the interconnecting struts in the first region (the filtering region) has a transverse dimension less than the transverse dimension of the region having the interconnecting struts in the mounting region.

In the embodiment of FIG. 22, the filter strut portions and mounting strut portions each divide into connecting struts of half the width. In an alternate embodiment, the filter struts and mounting struts are also bifurcated, however the width of the connecting strut is increased so it is greater than one half the width of the struts and can for instance be equal to the width of the strut. Such bifurcation with increased width is also applicable to the other embodiments of the filter described herein. Bifurcation with decreased width is also contemplated.

Figure 20F:
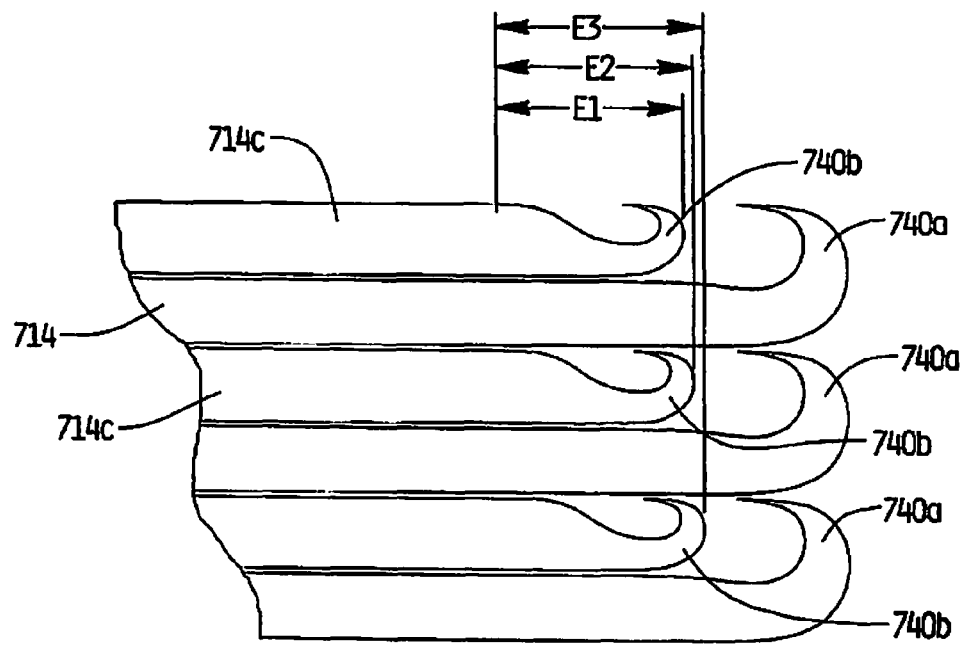
FIG. 20F is an enlarged developed view of the end portion of the filter of FIG. 20D showing the axial relationship of the retention hooks.
Figure 27:
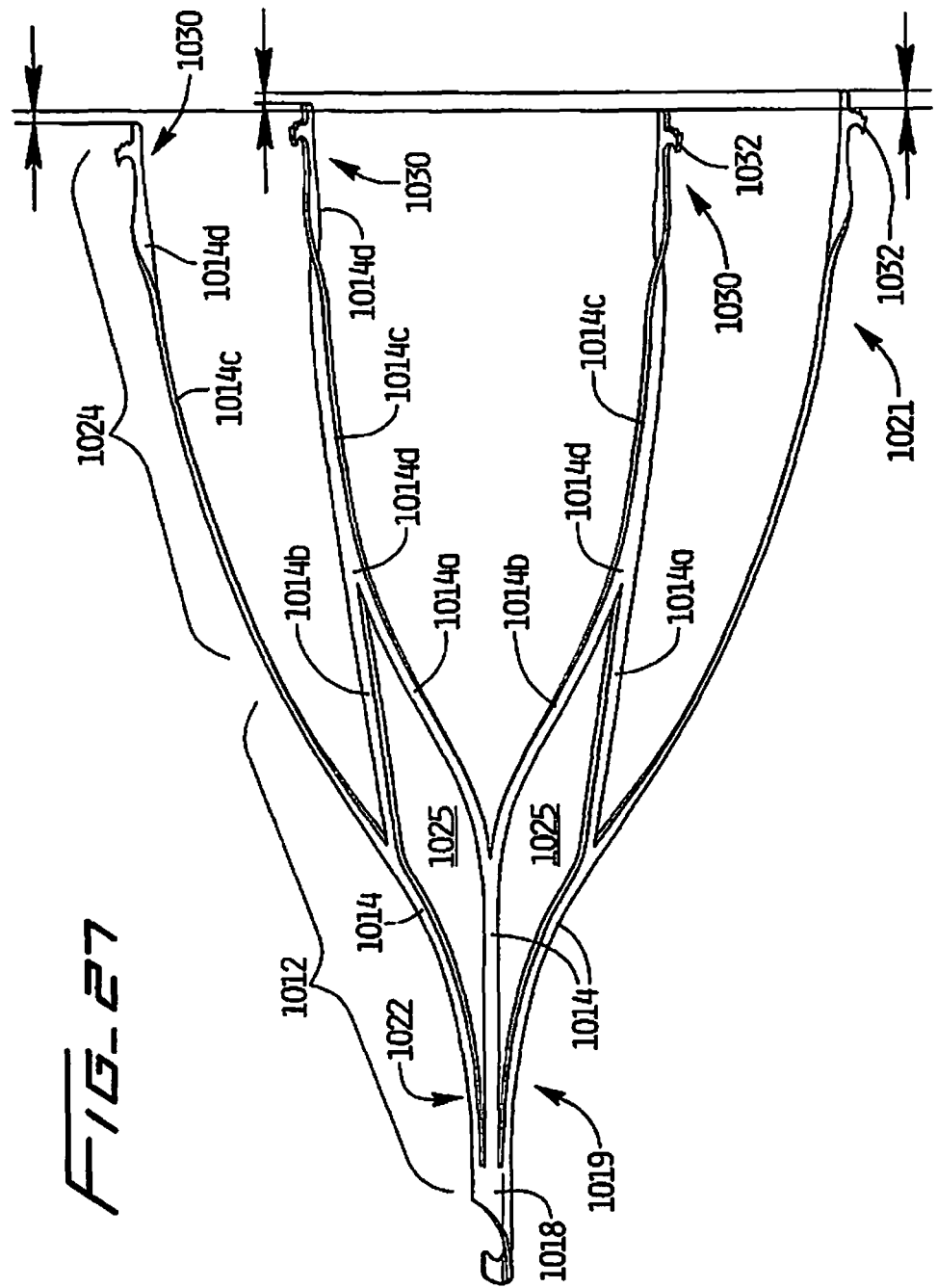
FIG. 27 is a side view of the filter of FIG. 25 showing the axial spacing of the retention hooks.

Preferably, the strut portions 914c terminate in hooks 940a, 940b similar to hooks 302a, 302b of FIG. 11D. That is, hooks 940a and 940b lie in the plane of the struts 914 and hooks 940a are larger than hooks 940b, formed so they occupy a region equivalent to the transverse dimension of two adjacent struts. Smaller hooks 940b nest within larger hooks 940a in the same manner as described above in conjunction with hooks 302a, 302b. Note that smaller hooks 940b are spaced axially (inwardly) of hooks 940a as well as spaced axially with respect to each other in the same manner as described with respect to hooks 740b of filter 700 and illustrated in FIG. 20F showing the three different distances E1, E2 and E3 in the developed view. Other hook designs could alternatively be provided, including the various hook embodiments described herein.

The tubular portion 918 is preferably in the form of a retrieval hook 950 as described herein with respect to the other embodiments, and preferably in the form of retrieval hook 290 of FIG. 13F. Other retrieval structure can also be utilized.

Filters 700, 800 and 900 are preferably manufactured from a cut tube, preferably laser cut. Therefore, as in the other embodiments described herein, terms such as interconnected, connected, joined, etc., are used for ease of description, it being understood that preferably these portions are integral as they are preferably formed from a single tube. Also, mounting struts and filter struts used to describe the various embodiments disclosed herein can be considered as mounting strut "portions" or "sections" and filter strut "portions" or "sections" of the same struts if the filter is formed integrally, e.g. from a cut tube.

The foregoing filters can be inserted through the femoral vein or alternatively through the internal jugular vein. It can be removed from access through the internal jugular vein or femoral vein. Various methods can be used to remove the filter such as those described in commonly assigned application Ser. No. 09/911,097, filed Jul. 23, 2001, now published application 2002-0193827-A1, published Dec. 19, 2001, the entire contents of which is incorporated herein by reference, including for example, slotted hooks, graspers, etc. A recess or cutout can also be provided at the tubular end portions to receive a snare or other device for removal. A hook 222 at tubular portion 220 is illustrated in the embodiment of FIG. 13A and is configured to receive a snare. FIG. 13B illustrates another embodiment of a hook. Hook 232 formed in tubular portion 230 forms a cutout 234 for receiving a snare or other removal device. The snare can surround and grasp both ears 235. However, the gap 237 between the ears 235 also enables a retrieval snare to lie in the gap 237 to surround and grasp one of the two ears 235.

In the alternate embodiment of FIGS. 13C and 13D, hook 272 is similar to hook 232 of FIG. 13B in that it has two ears 275 with a gap 277 therebetween. However it differs in that it has a bottom cutout 278 formed between walls 279. It also differs in that surfaces 274 of ears 275 are rounded and outer proximal walls 278a angle outwardly (proximally) to curved peak 276 then angle inwardly (wall 278b) to provide a smoother transition into the retrieval sheath. Thus, two angled transitions are provided.

In the alternate embodiment of FIG. 13E, to further enhance the transition to facilitate withdrawal into the retrieval sheath, the side walls 284 extending into ears 285 of hook 282 angle inwardly toward the longitudinal axis. Consequently, there are three angled transitions: 1) an angled transition in a first direction formed by angled walls 288a which angle proximally outwardly from the edge 285a of ears 285 to the curved peak 285b (the proximal end of the hook is designated generally by reference numeral 283); 2) an angled transition in a second direction formed by angled walls 288b which angle distally outwardly from curved peak 285b; and 3) an angled transition formed by walls 284 which angle proximally inwardly as walls 284 come closer together toward the proximal end. This results in a smoother transition into the retrieval sheath as it reduces the likelihood of the filter proximal end, i.e. the hook, being caught on the edge of the sheath—the angled edges which create camming surface for all approaches of the filter (360 degree range) will help the hook edges slide into the sheath.

FIGS. 13F and 13G illustrate another alternate embodiment of the retrieval hook of the present invention. This is the retrieval hook shown in conjunction with filter 301 of the embodiment of FIGS. 11D and 11G. Hook 290 has a curved hook 292 at the proximalmost end. This hook 292 is configured to receive a retrieval snare or other retrieval device. A portion of the wall of the hook 290 is cut out to expose the annular interior surface 294. That is, being formed from a laser cut tube, a wall portion is removed to expose curved inner wall surface 294. This annular interior surface 294 extends from radiused region 295 to proximalmost edge 296. The interior surface 294, for ease of explanation, can be considered to have an interior surface 294a at the radiused region 295 and an interior surface 295b at the hook 292. The interior surface 294b accommodates a portion of a tubular snare sheath. That is, the outer wall of the snare sheath (tube) can partially fit within the cut out region 293. This enhances removal as the snare pulls the filter hook into collinear arrangement with the sheath tube. This can be appreciated by reference to FIGS. 13H-13J discussed below. The radiused region 295, spaced axially (distal) from the hook 292, includes a radiused or curved edge defined by radiused side walls 297a, 297c and top wall 297b. The angled side walls 297a, 297c form camming surfaces to direct the hook 290 and filter into the retrieval sheath. This can be appreciated by reference to FIGS. 13K-13N discussed below.

It should be appreciated, that the hook can be formed in other ways to provide an interior annular surface to function in a similar manner as surface 294, i.e. to receive the snare tube.

It should be appreciated that any of the retrieval hooks can be used with any of the filters described herein.

In FIGS. 13H-13J, the snare approaches the retrieval hook 290 in the orientation shown. This results in a collinear arrangement. More specifically, the snare 502 is part of a retrieval system which includes a snare sheath or tube 504 through which the snare 502 extends. The distal wall 503 of snare sheath 504 provides for cinching of the snare 502. The snare sheath 504 is inserted through retrieval sheath 510. When the filter is pulled into the retrieval sheath 510 it is collapsed for removal. As discussed above, preferably cold saline is injected during the removal process to cool the sheath to transition to a softer martensitic state to facilitate removal.

In the orientation shown, as snare 502 retracts the filter, the snare sheath 504 fits into the cut out region 293 as its outer wall conforms to the inner wall surface 294b of hook 292. Thus, the hook 290 and snare sheath 504 become substantially collinear as shown in FIG. 13I. This collinear arrangement facilitates retraction into the retrieval sheath 510 as it reduces the likelihood of a wall of the hook getting caught on the distal edge 512 of the retrieval sheath 510, thus providing a smoother transition into the sheath as shown in FIG. 13J.

FIGS. 13K-13N illustrate the retrieval steps when the snare approaches from the opposite orientation of FIG. 13H, i.e. below the hook as viewed in the orientation of FIG. 13K. As the snare 502 retracts the filter towards the sheath 510, the wall 297b contacts the edge 512 of retrieval sheath 510 and due to the radiused walls 297a, 297c (depending on the side of contact), the hook is cammed downwardly (in the orientation of FIG. 13M) into the retrieval sheath 510 as shown in FIG. 13N. This provides a smooth transition into the retrieval sheath 510 as it reduces the likelihood of the hook being caught on the sheath edge.

FIG. 12A illustrates another embodiment having a series of recesses 210 along the length of the tubular portion 212. This enables the tubular portion 212 to be grasped at several locations along its length, facilitating grasping of the filter for removal. These multiple recesses or cutouts 210 are axially spaced as shown. In the embodiment of FIG. 12B, the end of the tubular portion 240 has a series of axially spaced cutouts 242 which form a coil-like engagement structure. This engagement structure provides multiple engagement areas for a retrieval (removal) device, such as a retrieval snare, for grasping the filter as the device can for instance be cinched in any of the spaces (formed by the cutouts) between the turns 246 in the helical coil. FIG. 12C shows a snare 300 placed in one of the cutouts 242.

To facilitate removal of the filter from the vessel, cold saline can be injected onto the implanted filter to change the temperature of the filter to move it to a relatively softer condition to facilitate the filter being drawn in to the retrieval sheath. That is, injection of cold saline will cause the filter to approach its martensitic state, bringing the filter to a more flexible condition. The flexible condition facilitates the collapse and withdrawal of the filter into the retrieval sheath, by decreasing the frictional contact between the filter and the inner surface of the retrieval sheath.

A delivery system for the filter of the present invention is shown in FIGS. 17 and 18. The delivery system 600 includes a hub 602, a cartridge 604 containing the filter, a pusher 606 and a wire 608 extending through the pusher 606. The wire 608 extends through the cartridge 604 and through the length of tube 603 to maintain a separation of the hooks, e.g. hooks 402 of filter 350 of FIG. 11G, during insertion of the delivery system and delivery of the filter. The cartridge 604 is removably attached to the hub 602, preferably by a snap-fit although other modes of attachment are also contemplated. The cartridge preferably has markings (not shown) on the outer surface to indicate a femoral or jugular direction so the user knows the orientation to attach the cartridge 604 to hub 602.

Once attached, advancement of the pusher 604 advances the filter from the cartridge and through tube 603 as the distal edge of the pusher 604 abuts the proximal end of the filter, with the wire 608 (e.g., a Nitinol wire) preventing entanglement of the retention hooks. The wire 608 also provides support (stability) for the pusher 604 as the pusher 604 is advanced over the wire 608. The filter is forced out of the distal end of the tube, where it is no longer cooled by saline and is warmed by body temperature to return toward its memorized configuration.

To enhance the retention of the cartridge 604 in the hub 602, a locking mechanism can be provided such as the mechanism of FIG. 19. The cartridge 604 has a pair of locking rails 612a, 612b, each including a respective recess 614a, 614b. The hub 602 contains a detent 620 as shown. When the cartridge 604 is inserted into the hub 602, the recess 614a of the locking rails 612a is retained by the detent 620. This locks the cartridge 604 to the hub 602 during use, preventing unwanted separation of the cartridge 604 from the hub 602. If access via the jugular artery instead of the femoral artery is desired, then the cartridge is inserted so that recess 614b of rail 612b engages detent 620 of hub 602.

While the above description contains many specifics, those specifics should not be construed as limitations on the scope of the disclosure, but merely as exemplifications of preferred embodiments thereof. For example, the filters can be inserted in other regions of the body. Also, any of the aforedescribed filters can have mounting sections of varying thickness. The foregoing filters can be made of materials other than shape memory material. Those skilled in the art will envision many other possible variations that are within the scope and spirit of the disclosure as defined by the claims appended hereto.

What is claimed is:

1. A vessel filter comprising a tubular region and a plurality of elongated filter struts extending initially linearly distally from the tubular region and then angling radially outwardly from a longitudinal axis of the filter to diverge, the plurality of elongated filter struts including at least first, second and third elongated filter struts, the first elongated filter strut separating into diverging first and second connecting struts which extend therefrom in different directions, the second elongated filter strut separating into diverging third and fourth connecting struts extending therefrom in different directions, the first and third connecting struts converging at a first joining region to form a first four sided closed geometric shape and the second connecting strut converging at a second joining region with a fifth connecting strut diverging from the third elongated filter strut to form a second four sided closed geometric shape, the first and second geometric shapes formed in a filter region of the filter, a transverse dimension at the joining regions of the connecting struts being greater than a transverse dimension at the tubular region, and an elongated mounting strut extending from each of the joining regions and being unconnected along their length.

2. The vessel filter of claim 1, wherein the elongated mounting struts further comprise a vessel engaging hook extending therefrom.

3. The vessel filter of claim 2, wherein the elongated mounting struts terminate in the vessel engaging hooks.

4. The vessel filter of claim 1, wherein the vessel filter has a midpoint, and a region wherein the first and second elongated filter struts separate is proximal of the midpoint.

5. The vessel filter of claim 1, wherein the first and second closed geometric shapes are substantially diamond shaped.

6. The vessel filter of claim 1, wherein the tubular region has a cutout formed therein to form a retrieval hook.

\* \* \* \* \*